(12) United States Patent
Numata et al.

(10) Patent No.: US 10,723,806 B2
(45) Date of Patent: *Jul. 28, 2020

(54) METHOD OF INTRODUCING NUCLEIC ACID INTO PLANT CELLS

(71) Applicant: RIKEN, Wako-shi, Saitama (JP)

(72) Inventors: Keiji Numata, Saitama (JP); Takeshi Yoshizumi, Saitama (JP); Yutaka Kodama, Tochigi (JP); Misato Ohtani, Saitama (JP); Taku Demura, Saitama (JP)

(73) Assignee: Riken, Saitama (JP)

( * ) Notice: Subject to any disclaimer, the term of this patent is extended or adjusted under 35 U.S.C. 154(b) by 962 days.

This patent is subject to a terminal disclaimer.

(21) Appl. No.: 14/381,045

(22) PCT Filed: Feb. 27, 2013

(86) PCT No.: PCT/JP2013/056062
§ 371 (c)(1),
(2) Date: Aug. 26, 2014

(87) PCT Pub. No.: WO2013/129698
PCT Pub. Date: Sep. 6, 2013

(65) Prior Publication Data
US 2015/0218569 A1    Aug. 6, 2015

Related U.S. Application Data

(60) Provisional application No. 61/691,833, filed on Aug. 22, 2012.

(30) Foreign Application Priority Data

Feb. 27, 2012  (JP) ................................. 2012-040622

(51) Int. Cl.
C07K 7/06       (2006.01)
C07K 19/00      (2006.01)
C12N 15/82      (2006.01)

(52) U.S. Cl.
CPC ............... *C07K 19/00* (2013.01); *C07K 7/06* (2013.01); *C12N 15/8206* (2013.01)

(58) Field of Classification Search
None
See application file for complete search history.

(56) References Cited

U.S. PATENT DOCUMENTS

| 9,334,494 B2 * | 5/2016 | Basu ................. | C12N 15/1089 |
| 2007/0275923 A1 * | 11/2007 | Chen .................... | C12N 15/111 514/44 A |
| 2007/0292909 A1 | 12/2007 | Miyawaki et al. | |
| 2009/0176710 A1 * | 7/2009 | Hadwiger .......... | A61K 48/0008 514/12.2 |
| 2011/0035836 A1 * | 2/2011 | Eudes ................ | C12N 15/8206 800/278 |

FOREIGN PATENT DOCUMENTS

| EP | 0665290 A2 | 8/1995 |
| JP | 07-213285 A | 8/1995 |
| JP | 2010-532159 A | 10/2010 |
| WO | WO 2005/054464 A1 | 6/2005 |
| WO | WO 2008/148223 A1 | 12/2008 |
| WO | WO 2009/079635 A1 | 6/2009 |
| WO | WO 2011/006133 A2 | 1/2011 |

OTHER PUBLICATIONS

Eggenberger et al (Using the Peptide Bp100 as a Cell-Penetrating Tool for the Chemical Engineering of Actin Filaments within Living Plant Cells. ChemBioChem 12:132-137, 2011).*
Unnamalai et al (Cationic oligopeptide-mediated delivery of dsRNA for post-transcriptional gene silencing in plant cells. FEBS Letters 566: 307-310, 2004).*
Ishihara et al (Intracellular delivery of siRNA by cell-penetrating peptides modified with cationic oligopeptides. Drug Delivery, 16(3): 153-159, 2009) (Year: 2009).*
Unnamalai et al (Cationic oligopeptide-mediated delivery of dsRNA for post-transcriptional gene silencing in plant cells. FEBS Letters 566: 307-310, 2004). (Year: 2004).*
Eggenberger et al (Using the Peptide Bp100 as a Cell-Penetrating Tool for the Chemical Engineering of Actin Filaments within Living Plant Cells. ChemBioChem 12:132-137, 2011). (Year: 2011).*
Eggenberger et al., "Using the Peptide Bp100 as a Cell-Penetrating Tool for the Chemical Engineering of Actin Filaments within Living Plant Cells," ChemBioChem, 2011, 12:132-137.
Hatefi et al., "Recombinant polymer-protein fusion: a promising approach towards efficient and targeted gene delivery," The Journal of Gene Medicine, 2006, 8:468-476.
Numata et al., "Mass production of bio-substance by development of selective organelle transformation method," http://www.nedo.go.jp/content/100166084.pdf, Aug. 25, 2011, with English translation, 3 pages.
Supplementary European Search Report dated Sep. 29, 2015, in EP 13755612.2.
Lakshmanan et al., "Rapid and Efficient Gene Delivery into Plant Cells Using Designed Peptide Carriers," Biomacromolecules, Jan. 14, 2013, 14(1):10-16.
Eggenberger et al., "Passage of Trojan Peptoids into Plant Cells," ChemBioChem, 2009, 10:2504-2512.
Office Action dated Aug. 29, 2017, in JP 2014-502429.

* cited by examiner

*Primary Examiner* — Medina A Ibrahim
*Assistant Examiner* — Wayne Zhong
(74) *Attorney, Agent, or Firm* — Foley & Lardner LLP

(57) ABSTRACT

The object of the present invention is to provide a method of introducing a nucleic acid into plant cells, which is simple and widely applicable to various types of plant cells and nucleic acids. The present invention relates to a method of introducing a nucleic acid into a target plant cell, comprising a step of forming a complex by bringing a carrier peptide, wherein the carrier peptide comprises a cell-penetrating sequence and a polycationic sequence, into contact with a nucleic acid and a step of bringing the obtained complex into contact with a target plant cell.

11 Claims, 9 Drawing Sheets

Specification includes a Sequence Listing.

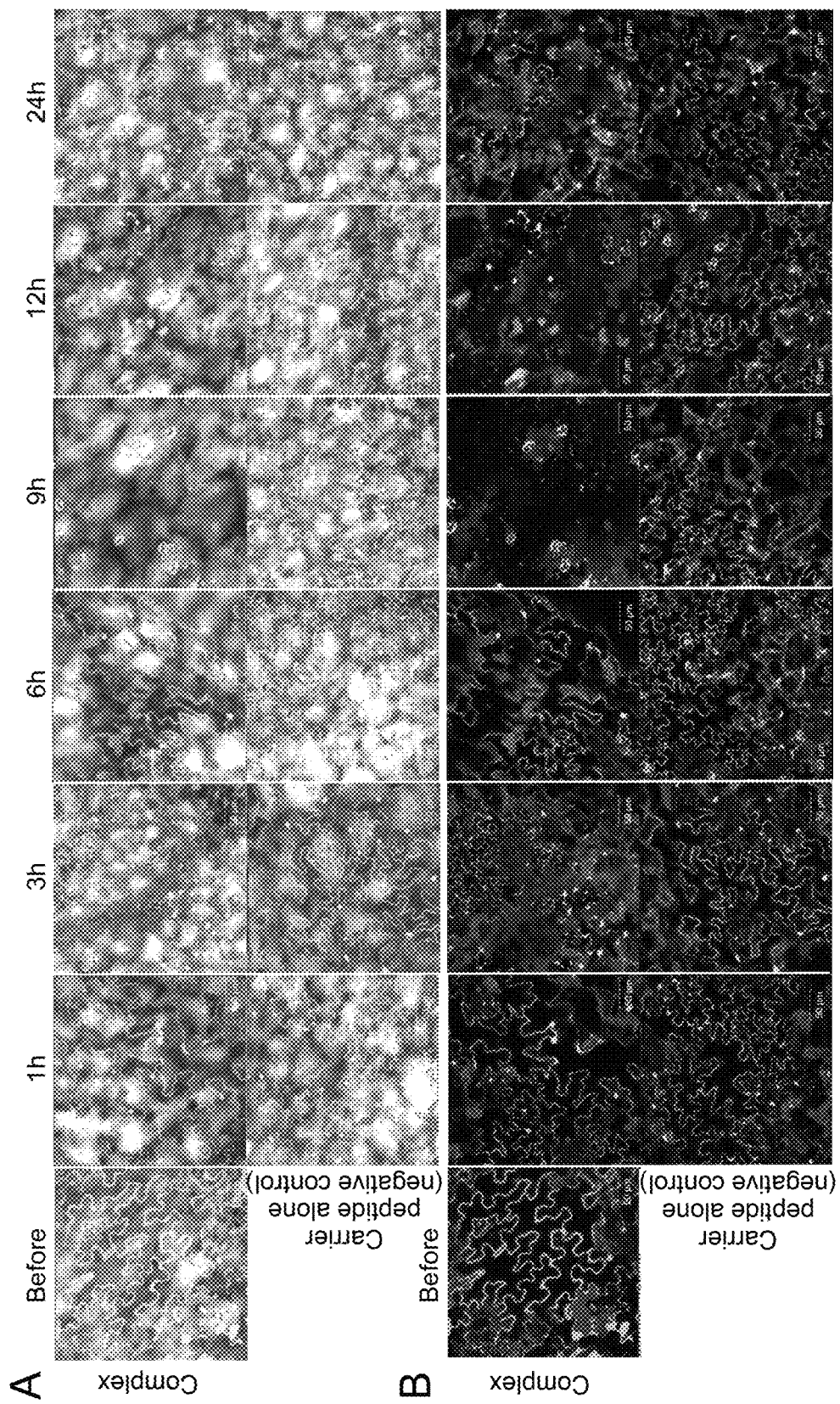

METHOD OF INTRODUCING NUCLEIC ACID INTO PLANT CELLS

CROSS-REFERENCE TO RELATED APPLICATIONS

This application is a National Stage application of PCT/JP2013/056062, filed Feb. 27, 2013, which claims priority from Japanese application JP 2012-040622, filed Feb. 27, 2012, and U.S. Provisional Application No. 61/691,833, filed Aug. 22, 2012.

The instant application contains a Sequence Listing which has been submitted in ASCII format via EFS-WEB and is hereby incorporated by reference in its entirety. Said ASCII copy, created on Aug. 23, 2019, is named 081356-0439 SL.txt and is 23,165 bytes in size.

TECHNICAL FIELD

The present invention relates to a method of introducing a nucleic acid into a plant cell by use of a carrier peptide comprising a plurality of functional domains, a carrier peptide for use in the method, a kit for use in the method and a complex of the carrier peptide and a nucleic acid.

BACKGROUND ART

Providing useful traits that cannot be provided by cross breeding to a plant by introducing foreign genes to plant cells is extremely meaningful in future improvement of crops and development of agriculture. Furthermore, in order to establish a substance production method by plants using carbon dioxide as a raw material, as a novel substance production method alternating a petroleum-dependent substance production method, it is indispensable to use a plant genetic recombination technique.

As a method of introducing a gene into a plant cell, an *Agrobacterium* method using infection with a soil bacterium, i.e., *Agrobacterium*, a particle-gun method and a viral vector method are known. The *Agrobacterium* method is the most frequently used in introducing a gene into a plant cell. However, there are many economically important plants to which a gene cannot be introduced by the *Agrobacterium* method, at present. The particle-gun method has been much more generally used compared to the *Agrobacterium* method; however, device cost is high. In addition to this problem, there is a risk of damaging a gene and transformation efficiency is low. The viral vector method is advantageous compared to the *Agrobacterium* method since transformation efficiency and gene expression efficiency are high; however, the method has a problem in that the size of the gene to be introduced is limited and viral infectious ability is low. In the circumstances, it has been desired to develop a novel method of introducing a gene, which is simple and widely applicable to all types of plants and genes.

It is known that a cell-penetrating peptide (CPP) has a function of transporting a complex comprising the peptide and another substance (for example, a protein and a nucleic acid) through biomembrane of mammalian and human cell strains. However, use of CPP in plant cells is limited. Unlike animal cells, plant cells have double barriers, i.e., cell wall and cell membrane, for preventing internalization of a complex comprising CPP. In the meantime, it is disclosed that a polycationic peptide concentrates negatively charged DNA by ionic interaction to form a complex that can be used for gene delivery, and that such a complex is useful for introducing a gene into animal cells (Patent Document 1: WO2011/006133). It has been also reported that a polycationic peptide was used for introducing a gene into a plant protoplast (Patent Document 2: JP Patent Publication (Kokai) No. 7-213285). However, the method employs a protoplast without a cell wall. In addition, it cannot be said that gene introduction efficiency into a plant cell is sufficient, in this method.

PRIOR ART DOCUMENTS

Patent Documents

Patent Document 1: WO2011/006133
Patent Document 2: JP Patent Publication (Kokai) No. 7-213285

SUMMARY OF INVENTION

Problem to be Solved by the Invention

An object of the present invention is to provide a method of introducing a nucleic acid into plant cells, which is simple and widely applicable to various types of plant cells and nucleic acids.

Means for Solving the Problem

The present inventors combined a cell-penetrating sequence and a polycationic sequence to construct a fusion peptide serving as a carrier peptide, which was further combined with a nucleic acid to form a complex. As a result, they found that excellent transfection efficiency to a plant cell can be attained by the complex. Based on the finding, the present invention was accomplished.

More specifically, the present invention includes the following inventions.

(1) A method of introducing a nucleic acid into a target plant cell, comprising a step of forming a complex by bringing a carrier peptide, wherein the carrier peptide comprises a cell-penetrating sequence and a polycationic sequence, into contact with a nucleic acid and a step of bringing the obtained complex into contact with a target plant cell.

(2) The method according to (1), wherein the number of amine groups from the carrier peptide/the number of phosphate groups from the nucleic acid is 2 or less.

(3) The method according to (1) or (2), wherein the complex has an average hydrodynamic diameter of 150 to 500 nm.

(4) The method according to any one of (1) to (3), wherein the cell-penetrating sequence is BP100 or $Tat_2$.

(5) The method according to any one of (1) to (4), wherein the polycationic sequence comprises at least three amino acid residues selected from lysine (K), arginine (R) and histidine (H).

(6) The method according to (5), wherein the polycationic sequence comprises 3 to 20 repeat sequences of KH (SEQ ID NO: 45) or a sequence of 3 to 20 consecutive Rs (SEQ ID NO: 46).

(7) The method according to any one of (1) to (6), wherein the step of forming a complex is performed in the presence of a carrier peptide comprising an organelle transit sequence and a polycationic sequence.

(8) The method according to any one of (1) to (7), wherein the carrier peptide further comprises an organelle transit sequence.

(9) The method according to any one of (1) to (8), wherein incubation time for bringing the complex into contact with a target plant cell is 5 to 150 hours.

(10) A carrier peptide for introducing a nucleic acid into a target plant cell, comprising a cell-penetrating sequence and a polycationic sequence.

(11) The carrier peptide according to (10), wherein the cell-penetrating sequence is BP100 or $Tat_2$.

(12) The carrier peptide according to (10) or (11), wherein the polycationic sequence comprises at least three amino acid residues selected from lysine (K), arginine (R) and histidine (H).

(13) The carrier peptide according to any one of (10) to (12), wherein the polycationic sequence comprises 3 to 20 repeat sequences of KH (SEQ ID NO: 45) or a sequence of 3 to 20 consecutive Rs (SEQ ID NO: 46).

(14) The carrier peptide according to any one of (10) to (13), further comprising an organelle transit sequence.

(15) A complex for introducing a nucleic acid into a target plant cell, comprising the carrier peptide according to any one of (10) to (14) and a nucleic acid.

(16) A complex for introducing a nucleic acid into a target plant cell, comprising the carrier peptide according to any one of (10) to (13), a carrier peptide comprising an organelle transit sequence and a polycationic sequence, and a nucleic acid.

(17) The complex according to (15) or (16), wherein the number of amine groups from the carrier peptide/the number of phosphate groups from the nucleic acid is 2 or less.

(18) The complex according to any one of (15) to (17), wherein the complex has an average hydrodynamic diameter of 150 to 300 nm.

(19) A kit for introducing a nucleic acid into a target plant cell, which comprises a carrier peptide comprising a cell-penetrating sequence and a polycationic sequence.

(20) The kit according to claim 19, which further comprises a carrier peptide comprising an organelle transit sequence and a polycationic sequence.

(21) The kit according to (19) or (20), wherein the cell-penetrating sequence is BP100 or $Tat_2$.

(22) The kit according to any one of (19) to (21), wherein the polycationic sequence comprises at least three amino acid residues selected from lysine (K), arginine (R) and histidine (H).

(23) The kit according to any one of (19) to (22), wherein the polycationic sequence comprises 3 to 20 repeat sequences of KH (SEQ ID NO: 45) or a sequence of 3 to 20 consecutive Rs (SEQ ID NO: 46).

Effects of the Invention

A method of introducing a nucleic acid into a plant cell, which is simple and widely applicable to various types of plant cells and nucleic acids, is provided by the present invention.

The present application claims the priority based on Patent Application No. 2012-040622 and provisional U.S. Patent Application No. 61/691,833, the contents (described in the specifications, claims and drawings) of which are incorporated herein by reference.

BRIEF DESCRIPTION OF DRAWINGS

FIG. 7A (the lower portion) shows epidermal cells of *Arabidopsis thaliana* L. leaf impregnated with a carrier peptide alone. YFP expression (yellow) and a DIC image are superposed and shown in the figure.

FIG. 8 (right) shows the results of Rluc expression in *Arabidopsis thaliana* L. to which a complex (which is prepared from a carrier peptide comprising a mitochondrial transit sequence and a plasmid comprising an Rluc gene) is introduced, and incubated by varying incubation time, in comparison with various incubation periods. The error bars indicate standard deviations of samples (n=4). Significant difference was observed between two groups at *p<0.05.

EMBODIMENTS FOR CARRYING OUT THE INVENTION

Figure 1:
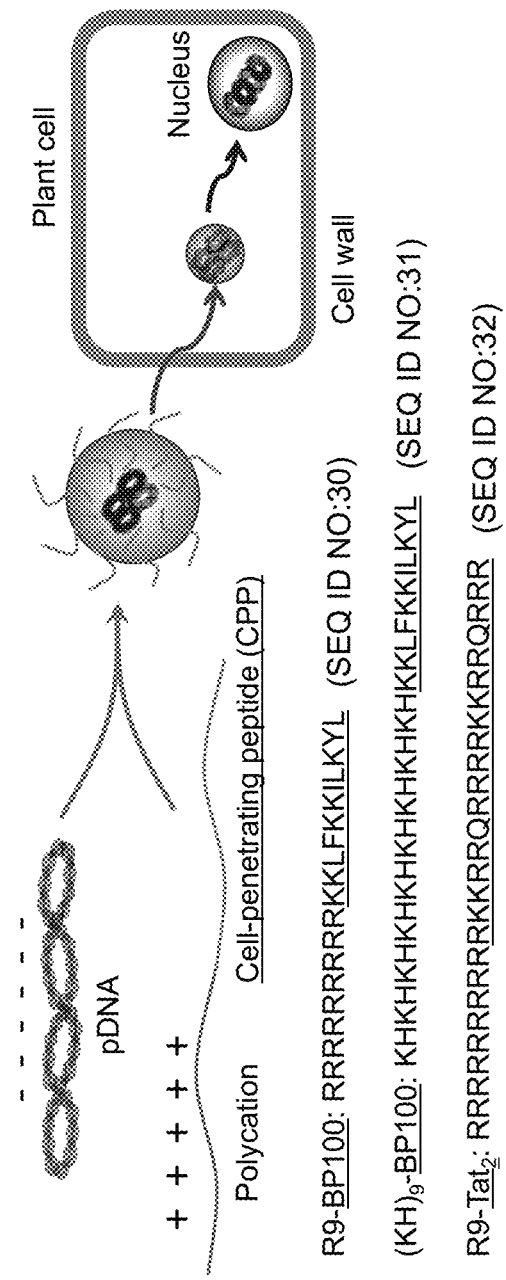
FIG. 1 is a schematic view illustrating a complex of a carrier peptide and a nucleic acid according to the present invention and introduction of the nucleic acid into a plant cell using the complex.

In an embodiment, the present invention relates to a method of introducing a nucleic acid into a target plant cell, which comprises a step of forming a complex by bringing a carrier peptide, which comprises a cell-penetrating sequence and a polycationic sequence, into contact with a nucleic acid and a step of bringing the obtained complex into contact with a target plant cell. The nucleic acid to be introduced into the target plant cell may be linear or circular; a single strand or a double strand; and DNA, RNA or a DNA/RNA hybrid. DNA includes a DNA molecule of any type and any size, such as cDNA, a plasmid, a genomic DNA and DNA containing a derivative thereof. In addition to this, the nucleic acid may be chemically modified as long as negative charge of its phosphate backbone, which mediates an ionic binding to a polycationic sequence of a carrier peptide, is maintained. Examples of a preferably modified nucleic acid include thioate and dithioate. In connection with this, other preferable nucleic acid derivatives are described, for example, in Uhlmann & Peymann, Chemical Reviews, 90 (4), 544-584, 1990.

Furthermore, a nucleic acid whose nucleotide base is chemically modified, can be used. For example, an RNA molecule having one to several nucleotides whose 2'-OH group is substituted with an O-alkyl group, a halogen or another modification group, can be used. The nucleic acid to be introduced into a target plant cell is preferably DNA or RNA which, if desired, may be modified. For example, the nucleic acid to be introduced into a target plant cell is allowed to contain genetic information that is to be expressed in the target plant cell. Owing to this method, for example, a gene-dependent defect can be removed. In contrast, the nucleic acid to be introduced into a target plant cell may have a property of anti-sense (in other words, the nucleic acid is a complementary nucleic acid to mRNA to be expressed in the target plant cell) in order to suppress expression of a predetermined gene in the target plant cell. The nucleic acid to be introduced into a target plant cell may have a property of a ribozyme, in other words, may have an ability to cleave a predetermined RNA molecule in a target plant cell. Examples of such a ribozyme include a hammer head ribozyme (Rossi & Sarver, Tibtech, 8, 179-183, 1990).

In the present invention, a silencing function can be expressed by introducing a complex of dsRNA and a carrier peptide into a target plant cell without decomposition of the dsRNA. Accordingly, gene expression can be temporarily controlled. Since this does not correspond to gene recombination, it can be carried out in the countries where recombinant crop is not allowed. For example, application as an agricultural chemical is possible.

The method of introducing a nucleic acid according to the present invention is characterized in that a nucleic acid can be introduced into a plant cell without any limitation in type and size. A short-chain RNA of about 20 base pairs to a double stranded DNA of about several hundreds of kilo base pairs can be used. More specifically, in the case of double stranded DNA, the size of the nucleic acid to be introduced is usually 20 base pairs to 20 K base pairs and preferably 50 base pairs to about 10 kilo base pairs.

In the specification, introduction of a nucleic acid into a plant cell will be described; however, the present invention can be applied to any cells including animal cells and cells having cell membrane. In the present invention, plant cells refer to cells except animal cells, in other words, cells having a cell wall. The types of plant cells are not particularly limited. The present invention can be applied to any plant cells such as angiosperm including monocotyledonous plants and dicotyledonous plants, gymnosperm, bryophyte, pteridophyte, herbaceous plant and woody plant. Specific examples of the plants include solanaceae [eggplant (*Solanum melongena* L.), tomato (*Solanum lycopersicum*), green pepper (*Capsicum annuum* L. var. *angulosum* Mill.), red pepper (*Capsicum annuum* L.), tobacco (*Nicotiana tabacum* L.), etc.], gramineous [rice (*Oryza sativa*), wheat (*Triticum aestivum* L.), barley (*Hordeum vulgare* L.), perennial ryegrass (*Lolium perenne* L.), Italian ryegrass (*Lolium multiflorum* Lam.), meadow fescue (*Festuca pratensis* Huds.), thor fescue (*Festuca arundinacea* Schreb.), orchardgrass (*Dactylis glomerate* L.), timothy (*Phleum pratense* L.), etc.], brassicaceae [thale cres (*Arabidopsis thaliana*), colza (*Brassica campestris* L.), Chinese cabbage (*Brassica pekinensis* Rupr.), cabbage (*Brassica oleracea* L. var. *capitata* L.), Japanese radish (*Raphanus sativus* L.), rape (*Brassica campestris* L., *B. napus* L.), etc.], leguminous [soy bean (*Glycine max*), adzuki bean (*Vigna angularis* Willd.), kidney bean (*Phaseolus vulgaris* L.), broad beans (*Vicia faba* L.), etc.], cucurbitaceae [cucumber (*Cucumis sativus* L.), melon (*Cucumis melo* L.), watermelon (*Citrullus vulgaris* Schrad.), pumpkin (*C. moschata* Duch., *C. maxima* Duch.) etc.], convolvulaceae [sweet potato (*Ipomoea batatas*), etc.], liliaceae [leek (*Allium fistulosum* L.), onion (*Allium cepa* L.), Chinese chive (*Allium tuberosum* Rottl.), garlic (*Allium sativum* L.), asparagus (*Asparagus officinalis* L.), etc.], lamiaceae [perilla (*Perilla frutescens* Britt. var. *crispa*), etc.], asteraceae [chrysanthemum (*Chrysanthemum morifolium*), garland chrysanthemum (*Chrysanthemum coronarium* L.), lettuce (*Lactuca sativa* L. var. *capitata* L.), etc.], rosaceae [rose (*Rosa hybrida* Hort.), strawberry (*Fragaria× ananassa* Duch.), etc.], rutaceae [mandarin orange (*Citras unshiu*), Japanese pepper (*Zanthoxylum piperitum* DC.), etc.], myrtaceae [eucalyptus (*Eucalyptus globulus* Labill), etc.], salicaceae [poplar (*Populas nigra* L. var. *italica* Koehne), etc.], chenopodiaceae [spinach (*Spinacia oleracea* L.), sugar beet (*Beta vulgaris* L.), etc.], gentianaceae [gentian (*Gentiana scabs* Bunge var. *buergeri* Maxim.), etc.] and caryophyllaceae [carnation (*Dianthus caryophyllus* L.), etc.]. Of them, solanaceae plants, particularly, tobacco, is preferably used.

As the plant cell, a cell derived from any plant tissue can be used and is not particularly limited. For example, plant cells derived from an embryo, a callus, a pollen, a leaf, an anther, a root, an apex of root, a flower, a seed, a sheath, a stem and a cultured tissue, can be used.

The carrier peptide to be used in the present invention is a peptide capable of forming a peptide-nucleic acid complex through ionic interaction with a nucleic acid and serving as a carrier, which facilitates introduction of a nucleic-acid into a plant cell. It is characterized in that the carrier peptide of the present invention comprises a cell-penetrating sequence and a polycationic sequence. In the present invention, the peptide may comprise a sugar chain, a lipid and/or a phosphate residue other than its peptide component.

The cell-penetrating sequence refers to a sequence of a cell-penetrating peptide (CPP). Examples of the cell-penetrating peptide include, but not limited to, BP 100 (Appl Environ Microbiol 72 (5), 3302, 2006), HIV Tat (Journal Biological Chemistry, 272, pp. 16010-16017, 1997), Tat$_2$ (Biochim Biophys Acta 1768 (3), 419, 2007), Penetratin, pVEC, pAntp (Journal Biological Chemistry, 269, pp. 10444-10450, 1994), HSV-1 VP22 (Cell, 88 pp. 223-233, 1997), MAP (Model amphiphilic peptide) (Biochimica Biophysica Acta, 1414, pp. 127-139, 1998), Transportan (FEBS Journal, 12, pp. 67-77, 1998), R7 (SEQ ID NO: 47) (Nature Medicine, 6, pp. 1253-1257, 2000), MPG (Nucleic Acid Research 25, pp. 2730-2736, 1997) and Pep-1 (Nature Biotechnology, 19, pp. 1173-1176, 2001). These peptide sequences having substitution, insertion and/or deletion of one to several amino acid residues can be favorably used in some cases. As the cell-penetrating peptide, two or more types of cell-penetrating peptides may be used in combination. The carrier peptide may comprise two or more types of cell-penetrating sequences. It is also preferable that a cell-penetrating peptide specific to a predetermined target cell is selected.

Specific examples of the cell-penetrating sequence include the following sequences:

KKLFKKILKYL, (SEQ ID NO: 1)

RKKRRQRRRRKKRRQRRR, (SEQ ID NO: 2)

RKKRRQRRR, (SEQ ID NO: 3)

PLSSIFSRIGDP, (SEQ ID NO: 4)

PISSIFSRTGDP, (SEQ ID NO: 5)

AISSILSKTGDP, (SEQ ID NO: 6)

PILSIFSKIGDL, (SEQ ID NO: 7)

PLSSIFSKIGDP, (SEQ ID NO: 8)

PLSSIFSHIGDP, (SEQ ID NO: 9)

PLSSIFSSIGDP, (SEQ ID NO: 10)

RQIKIWFQNRRMKWKK, (SEQ ID NO: 11)

DAATATRGRSAASRPTERPRAPARSASRPRRPVD, (SEQ ID NO: 12)

AAVALLPAVLLALLAP, (SEQ ID NO: 13)

AAVLLPVLLAAP, (SEQ ID NO: 14)

VTVLALGALAGVGVG, (SEQ ID NO: 15)

GALFLGWLGAAGSTMGA, (SEQ ID NO: 16)

MGLGLHLLVLAAALQGA, (SEQ ID NO: 17)

LGTYTQDFNKFHTFPQTAIGVGAP, (SEQ ID NO: 18)

GWTLNSAGYLLKINLKALAALAKKIL, (SEQ ID NO: 19)

KLALKLALKALKAALKLA. (SEQ ID NO: 20)

The polycationic sequence is a peptide sequence comprising at least three amino acid residues selected from lysine (K), arginine (R) and histidine (H) and forming a stable bond with a nucleic acid under physiological conditions. A polycation component may comprise a neutral amino acid other than positively charged amino acid residues (cationic amino acid residue) such as lysine, arginine and histidine, as long as cationic property is sufficiently maintained as a whole and a stable bond can be formed with a nucleic acid under physiological conditions. This can be examined by a simple experiment performed by adding a nucleic acid. For example, agarose gel electrophoresis is mentioned. In the electrophoresis, if a peptide-nucleic acid complex is sufficiently stable enough to cause retardation of a nucleic acid band, the peptide used in the complex is suitable. The retardation of the nucleic acid band indicates that a peptide-nucleic acid complex is maintained during agarose gel electrophoresis.

The polycationic sequence of the carrier peptide must comprise at least three amino acid residues selected from lysine, arginine and histidine; however, an upper limit of the number of the amino acid resides contained in the polycationic sequence cannot be determined. The polycationic sequence can comprise at most 450 amino acid residues. Even in this state, the polycationic sequence is known to be functional (Proc Natl Acad Sci USA 87, 3410-3414, 1990). However, the polycationic sequence preferably has a length corresponding to 5 to 100 amino acid residues, more preferably 5 to 50 and further preferably 7 to 20 amino acid residues. The ratio of cationic amino acid residues in the polycationic sequence is preferably 40 mol % or more, more preferably 60 mol % or more, further preferably 80 mol % or more and the most preferably 90 mol % or more. A polycationic sequence consisting of polycationic amino acid residues alone is most preferably used.

The polycationic sequence comprises lysine, arginine and/or histidine residues of preferably 4 or more, more preferably 5 or more and further preferably 7 or more; and preferably 30 or less, more preferably 25 or less and further preferably 20 or less. Furthermore, the polycationic sequence preferably has a continuous series of 3 or more residues of lysine, arginine and/or histidine residue, more preferably, a continuous series of 5 or more residues of lysine, arginine and/or histidine and particularly preferably, a continuous series of 7 or more residues of lysine, arginine and/or histidine residue, lithe ratio of arginine in the cationic amino acid residues is high, introduction into a cell tends to be facilitated; whereas, if the ratio of histidine and lysine is high, introduction into a cell tends to be slow. For example, the introduction rate of a complex into a cell can be controlled by appropriately selecting a polycationic sequence depending upon the intended use of the complex of the present invention such as an organelle specific introduction as described below. Examples of the polycationic sequence include KH repeat sequences [preferably 3 to 20 repeat sequences of KH (SEQ ID NO: 45), more preferably 5 to 15 repeat sequences of KH (SEQ ID NO: 48) and further preferably 7 to 12 repeat sequences of KH (SEQ ID NO: 49)], an arginine (R) continuous sequence, [for example, a sequence of 3 to 20 consecutive Rs (SEQ ID NO: 46), preferably a continuous sequence of 5 to 15 R (SEQ ID NO:

50) and further preferably a continuous sequence of 7 to 12 R (SEQ ID NO: 51)], a lysine (K) continuous sequence [for example, a continuous sequence of 3 to 20 K (SEQ ID NO: 52), preferably a continuous sequence of 5 to 15 K (SEQ ID NO: 53) and further preferably a continuous sequence of 7 to 12 K (SEQ ID NO: 54)]; and a histidine (H) continuous sequence [for example, a continuous sequence of 3 to 20 H (SEQ ID NO: 55), preferably a continuous sequence of 5 to 15 H (SEQ ID NO: 56) and further preferably a continuous sequence of 7 to 12 H (SEQ ID NO: 57)].

Specific examples of the polycationic sequence include the following sequences:

```
RRRRRR,                    (SEQ ID NO: 21)

KHKHKHKHKHKHKHKHKH.        (SEQ ID NO: 22)
```

The carrier peptide of the present invention comprises a structural component corresponding to a linear fusion of a cell-penetrating sequence and a polycationic sequence. In the fusion, it is preferable that the polycationic sequence is bound to the N-terminal and/or C-terminal of the cell-penetrating sequence. To the cell-penetrating sequence, one or more polycationic sequences, preferably one to several, more preferably, one to three and particularly preferably, one polycationic sequence can be bound. Binding can be chemically made in accordance with a general peptide binding reaction or biologically made using an enzyme such as ligase. For example, binding can be made in accordance with a general peptide synthesis method such as a solid phase method. In binding a cell-penetrating sequence to a polycationic sequence, e.g., an appropriate oligo peptide linker can be interposed between them. For example, a linker consisting of one to several amino acids can be interposed. The amino acid residues constituting the linker can be appropriately selected. Since the characteristics of a cell-penetrating peptide are shown by the N-terminal, the cell-penetrating sequence is preferably bound to the N-terminal of the polycationic sequence. The carrier peptide of the present invention can be obtained by a recombinant DNA technique. For example, a polycationic sequence-encoding DNA fragment is bound to one or both ends of a cell-penetrating sequence-encoding DNA fragment by a linkage reaction with an appropriate DNA adaptor or by in vitro mutagenesis. Such a gene manipulation method is known to those skilled in the art in the field of molecular biology.

The carrier peptide of the present invention can further comprise an organelle transit sequence in addition to a cell-penetrating sequence and a polycationic sequence. The organelle transit sequence refers to a peptide sequence having affinity for or permeability in an organelle within a cell. A peptide sequence having affinity for or permeability in a mitochondrion or a chloroplast is preferably used. To be described more specifically, examples thereof include, but not limited to, a chloroplast targeting peptide derived from *Chlamydomonas* ferredoxin (Cf) and *Chlamydomonas* Rubisco activase (CRa); a mitochondrial matrix targeting signal peptide (Biochemical and Biophysical Research Communications, 226, pp. 561-565, 1996); and mitochondrial inner membrane targeting signal peptides such as SS01, SS02, SS31, and SS20 (The AAPS Journal, 8, pp. E277-E283, 2006), 50S ribosome protein L28, 50S ribosome protein L24, 50S ribosome protein L27 and a RuBisCo small chain and LHCII type 1.

These peptide sequences having substitution, insertion and/or deletion of one to several amino acid residues can be favorably used in some cases. Of these, one or two or more types can be appropriately used in combination.

Formation of a complex by bringing a carrier peptide, which comprises cell-penetrating sequence and a polycationic sequence, into contact with a nucleic acid may be performed in the presence of another carrier peptide comprising an organelle transit sequence. In this case, the carrier peptide comprising an organelle transit sequence also preferably comprises a polycationic sequence. The carrier peptide comprising an organelle transit sequence and a polycationic sequence can form a complex with a nucleic acid, together with a carrier peptide comprising a cell-penetrating sequence and a polycationic sequence. The arrangement of the organelle transit sequence relative to the polycationic sequence is not limited; the organelle transit sequence is preferably bound to the C terminal of the polycationic sequence. The carrier peptide comprising an organelle transit sequence and a polycationic sequence as well as the carrier peptide comprising an organelle transit sequence, a polycationic sequence and a cell-penetrating sequence can be prepared by the same method as mentioned above.

Specific examples of the organelle transit sequence include:

```
                                    (SEQ ID NO: 23)
MAMAMRSTFAARVGAKPAVRGARPASRMSCMA, (SEQ ID NO: 24)
MQVTMKSSAVSGQRVGGARVATRSVRRAQLQV, (SEQ ID NO: 25)
MATMVAGISLRGPVMSSHRTFSVTKRASLPQSKLSSELSFVTSQLSGLKI

SSTHFISSSAPLSVPFKPSLQPVA, (SEQ ID NO: 26)
MAALQSSFAGLSTSFFGQRFSPPLSLPPLVKSTEGPCLIQA, (SEQ ID NO: 27)
MAVSFSLVGAFKGLSLASSSSFLKGDFGAAFPVAPKFSVSFPLKSPLTIE

S, (SEQ ID NO: 28)
MASSVLSSAAVATRSNVAQANMVAPFTGLKSAASFPVSRKQNLDITSIAS

NGGRVQC, (SEQ ID NO: 29)
MAASTMALSSPAFAGKAVKLSPAASEVLGSGRVTMRKTV, (SEQ ID NO: 44)
MLSLRQSIRFFK.
```

The nucleic acid introduced into a plant cell can be further introduced into a specific organelle within the cell by use of the carrier peptide comprising an organelle transit sequence. It is known that a mitochondrial genome and chloroplast genome have several tens to several thousands copies as large as those of a nuclear genome, and that if they are transformed as mentioned above, a foreign protein can be produced in a large amount. Accordingly, if the function of producing a substance that a plant has is used to the utmost limit by introducing a nucleic acid into a specific organelle in a cell, a bio-substance alternating a petroleum source and other useful substances can be produced in large amounts.

If a complex is formed of a carrier peptide comprising an organelle transit sequence and a polycationic sequence with a nucleic acid together with a carrier peptide comprising a cell-penetrating sequence and a polycationic sequence, the nucleic acid can be effectively introduced into a specific organelle in a cell. However, even if the carrier peptide comprising a cell-penetrating sequence and a polycationic sequence is not used; in other words, if a carrier peptide comprising an organelle transit sequence and a polycationic sequence alone is used, a nucleic acid can be introduced into a specific organelle in a cell by forming a complex with a nucleic acid.

In a step of forming a complex by bringing a carrier peptide into contact with a nucleic acid, it is preferable that they are brought into contact with each other such that the ratio of the number of amine groups from the carrier peptide and the number of phosphate groups from a nucleic acid (N/P ratio) becomes 2 or less and larger than 0.1. The N/P ratio is more preferably 0.2 or more, further preferably 0.3 or more and particularly preferably 0.4 or more. The N/P ratio is also more preferably 1.5 or less, further preferably 1.0 or less and particularly preferably 0.6 or less. The complex formed so as to have an N/P ratio of 0.5 is the most preferable. The present inventors found that a high transfection efficiency to a plant cell can be attained if a complex is formed by bringing a carrier peptide into contact with a nucleic acid so as to have such an N/P ratio. Note that if a carrier peptide comprising a cell-penetrating sequence and a polycationic sequence besides a carrier peptide comprising an organelle transit sequence are brought into contact with a nucleic acid, the number of amine groups from all carrier peptides is used a base.

In a step of forming a complex by bringing a carrier peptide and dsRNA into contact with each other, it is preferable that they are brought into contact with each other so as to have a molar ratio (carrier peptide/dsRNA) of 5 or less and larger than 0.1. The molar ratio is more preferably 0.5 or more and a further preferably 1 or more. Furthermore, the molar ratio is more preferably 5 or less and further preferably 2 or less. A complex formed so as to have a molar ratio of 1 to 2 is the most preferable. The present inventors found that transfection to plant cells can be made with a high efficiency and a high silencing effect can be attained if a complex is formed by bringing a carrier peptide and a dsRNA into contact with each other so as to have such a molar ratio.

The step of forming a complex by bringing a carrier peptide and a nucleic acid into contact with each other can be carried out, for example, by mixing the carrier peptide with the nucleic acid in a solution. In this case, the concentration of the carrier peptide is usually 10 µg/mL to 10 mg/mL and preferably 100 µg/mL to 1 mg/mL, and the concentration of the nucleic acid in the solution is usually 1 µg/mL to 10 mg/mL and preferably 10 µg/mL to 1 mg/mL.

A complex of a carrier peptide and a nucleic acid can be obtained by bringing the carrier peptide into contact with the nucleic acid, as described above, the binding mode between them and the configuration of the complex are not limited. The complex usually has a particle configuration and the average hydrodynamic diameter of the particle is preferably 150 nm or more, more preferably 200 nm or more and further preferably 300 nm or more; and preferably 500 nm or less, more preferably 400 nm or less and further preferably 350 nm or less. The average hydrodynamic diameter can be obtained based on the measurement by a dynamic light scattering (DLS) method. The present inventors found that a transfection to a plant cell can be made with a high efficiency by use of a complex having such an average hydrodynamic diameter.

The step of bringing the complex into contact with a target plant cell can be carried out in accordance with a method known in the art and is not particularly limited. For example, a target plant cell is impregnated with a solution of a carrier peptide/nucleic acid complex of the present invention, incubated in an incubator at a temperature of 20 to 35° C. under constant light irradiation for 14 to 18 hours per day. The incubation time is preferably 5 to 150 hours and more preferably 10 to 20 hours. The method of introducing a nucleic acid according to the present invention is particularly excellent since transfection is performed in a relatively short time.

The present invention also relates to a kit for introducing a nucleic acid into a target plant cell. It is characterized in that the kit of the present invention comprises a carrier peptide comprising a cell-penetrating sequence and a polycationic sequence. The kit of the present invention may further comprise a carrier peptide comprising an organelle transit sequence and a polycationic sequence. The kit may further comprise an operation manual and reagents and tools for forming a complex and introducing into a cell.

The present invention will be more specifically described based on the following Examples; however, the present invention is not limited by these Examples.

EXAMPLES (Example 1) Synthesis of Carrier Peptide

As a carrier peptide comprising a cell-penetrating sequence and a polycationic sequence,
R9-BP100 (RRRRRRRRRKKLFKKILKYL-NH$_2$ (SEQ ID NO: 30), theoretical pI/Mw: 12.55/2827.56 Da),
(KH)$_9$-BP100
(KHKHKHKHKHKHKHKHKHKKLFKKILKYL-NH$_2$ (SEQ ID NO: 31), theoretical pI/Mw: 10.81/3809.71 Da), and
R9-Tat$_2$
(RRRRRRRRRRKKRRQRRRRKKRRQRRR-NH$_2$ (SEQ ID NO: 32), theoretical pI/Mw: 13.28/3910.72 Da)
were synthesized by use of the standard 9-fluorenyl-methoxycarbonyl (Fmoc) solid phase peptide synthesis (G. B. Fields and R. L. Noble, Int J Pept Protein Res 35 (3), 161 (1990)).

Furthermore, carrier peptides comprising an organelle transit sequence and a polycationic sequence were prepared by combining chloroplast targeting peptides derived from *Chlamydomonas ferredoxin* (Cf) and *Chlamydomonas Rubisco activase* (CRa) with a polycationic sequence (KH)$_9$ (SEQ ID NO: 58). To be described more specifically,
Cf-(KH)$_9$ (MAMAMRSTFAARVGAKPAVRGARPAS-RMSCMAKHKHKHKHKHKH KHKHKH-NH$_2$ (SEQ ID NO: 33), theoretical pI/Mw: 12.20/5729.89 Da), and
CRa-(KH)$_9$ (MQVTMKSSAVSGQRVGGARVATRSVR-RAQLQVKHKHKHKHKHK KHKHKH-NH$_2$ (SD) ID NO: 34), theoretical pI/Mw: 12.62/5803.82 Da)
were synthesized by the solid phase peptide synthesis.

A polycationic sequence is underlined. These polypeptides are purified by high performance liquid chromatography (HPLC) and the molecule weights were determined by matrix-assisted laser desorption ionization flight time (MALDI-TOF) mass analysis. (KH)$_9$ (SEQ ID NO: 58), R9 (SEQ ID NO: 59) BP100 and Tat$_2$ were also synthesized for controls.

(Example 2) Preparation of Carrier Peptide-pDNA Complexes Different in N/P Ratio and Characterization Thereof Ionic complexes of carrier peptides (R9-BP100 and (KH)$_9$-BP100) different in N/P ratio and pDNA encoding a reporter gene were prepared and characterized by use of dynamic light scattering (DLS), an atomic force microscope (AFM), a zeta potential meter and agarose gel electrophoresis. The N/P ratio herein refers to the ratio of the number of amine groups from the carrier peptide and the number of phosphate groups from pDNA.

Two types of pDNA, i.e., green fluorescence protein (GFP)-encoding P35S-GFP (S65T)-TNOS and *Renilla* luciferase (RLuc)-encoding P35S-RLuc-TNOS, were used as reporter genes. All pDNA molecules were amplified in a competent DH5α *E. coli* (Takara) and purified by an Endofree Plasmid Giga Kit (Qiagen). To prepare a carrier peptide-pDNA complex, a carrier peptide (0.5 g/L) was mixed with a pDNA solution (about 1.0 mg/mL) so as to have different N/P ratios (0.5, 1, 2, 5, 10 and 20) at 25° C. Immediately after mixing, complexes were characterized by a zeta potential meter (Zetasizer Nano-ZS, Malvern Instruments Ltd) and an atomic force microscope (Seiko Instruments).

Solutions containing complexes each were diluted with ultra-pure water (MilliQ) up to a final volume of 800 μL and subjected to measurement of zeta potential and size. The zeta potential and zeta shift of the solution samples were measured three times by a zeta potential meter and averages of data were obtained by use of Zetasizer software ver 6.20 (Malvern Instruments Ltd). Dynamic light scattering (DLS) was performed to determine hydrodynamic diameters. Subsequently, polydispersion indexes (PDI) were determined by use of a zeta nanosizer (Zetasizer software ver 6.20) using He—Ne laser (633 nm) at 25° C. and a backscattering detection angle of 173°. Observation by an AFM was performed by fixing a complex solution on cut mica and using a silicon cantilever in air at room temperature in a tapping mode at a spring constant of 1.3 N/m. A cantilever tip rotation effect was obtained by calculation and true dimensions of complexes were obtained by the method previously reported (K. Numata, Y. Kikkawa, T. Tsuge et al., Macromol Biosci 6 (1), 41, 2006; K. Numata, T. Hirota, Y. Kikkawa et al., Biomacromolecules 5 (6), 2186, 2004). For gel retardation assay, each sample (40 μL) containing 1.0 μg of pDNA was mixed with a loading buffer, analyzed on a 1% agarose gel (TAE buffer, 100 V, 30 minutes) and stained with ethidium bromide.

According to the results of DLS (Table 1), the average hydrodynamic diameters of both R9-BP100-pDNA complex and $(KH)_9$-BP100-pDNA complex fall within the range of 0.1 to 20 and decrease as the N/P ratio increases. According to the average hydrodynamic diameter, a pDNA complex prepared so as to have an N/P ratio larger than 0.5 was successfully formed. In contrast, a pDNA complex prepared so as to have an N/P ratio of 0.1 showed a bimodal distribution, suggesting that the pDNA complex was non-uniformly formed. The diameters of complexes prepared so as to have an N/P ratio of 0.5 and 1 were about 300 nm; whereas complexes having an N/P ratio of 5, 10 and 20 had a diameter of about 120 nm.

TABLE 1

Size and PDI of R9-BP100-pDNA complex and $(KH)_9$-BP100-pDNA complex different in N/P ratio

| N/P ratio | R9-BP100 | | $(KH)_9$-BP100 | |
|---|---|---|---|---|
| | Size (nm) | PDI | Size (nm) | PDI |
| 0.1 | 508, 4720[a] | —[a] | 348, 4240[a] | —[a] |
| 0.5 | 319 | 0.34 | 291 | 0.31 |

TABLE 1-continued

Size and PDI of R9-BP100-pDNA complex and $(KH)_9$-BP100-pDNA complex different in N/P ratio

| N/P ratio | R9-BP100 | | $(KH)_9$-BP100 | |
|---|---|---|---|---|
| | Size (nm) | PDI | Size (nm) | PDI |
| 1 | 321 | 0.38 | 322 | 0.30 |
| 2 | 151 | 0.21 | 139 | 0.23 |
| 5 | 127 | 0.21 | 106 | 0.23 |
| 10 | 114 | 0.23 | 96 | 0.23 |
| 20 | 116 | 0.25 | 114 | 0.24 |

[a]Bimodal distribution, no significant PDI

Figure 2:
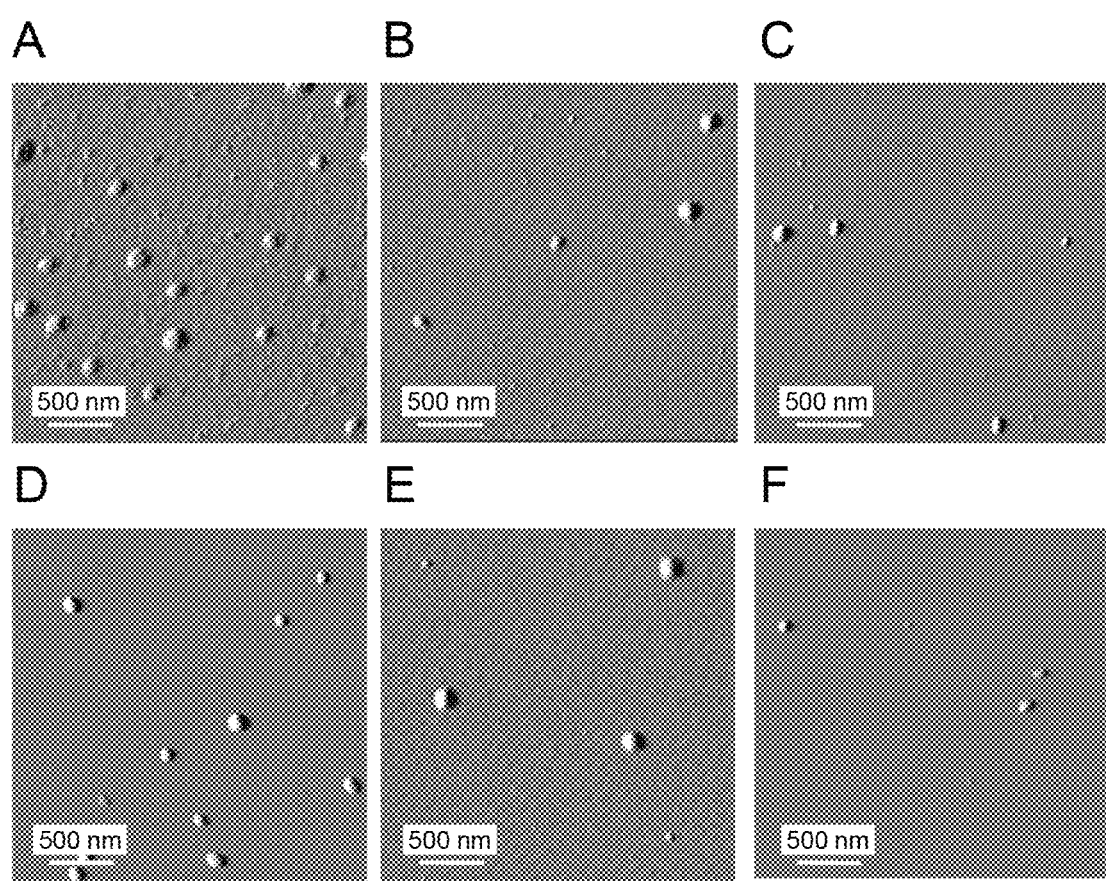
FIG. 2 shows AFM images of a carrier peptide-pDNA complex. A, B and C show AFM images of an R9-BP100-pDNA complex having an N/P ratio of 0.5, 1 and 20, respectively. D, E and F show AFM images of a $(KH)_9$-BP100-pDNA complex having an N/P ratio of 0.5, 1 and 20, respectively.

A pDNA complex was fixed onto mica and the configuration of the complex was observed by an AFM to make a picture (FIG. 2). All complexes had uniform spherical forms and pDNA complexes having an N/P ratio of 0.5, 1 and 20 had a width of 190±21 nm and a height of 12.8±5.3 nm; width of 98±17 nm and a height of 7.7±1.6 nm; and a width of 123±13 nm and a height of 9.1±2.2 nm (n=10), respectively. According to the volumes of pDNA complexes, the dimensions determined by DLS were slightly larger than those observed by the AFM. This is because pDNA complexes fixed on mica were dried in air to shrink (K. Numata, Y. Kikkawa, T. Tsuge et al., Macromol Biosci 6 (1), 41, 2006). As a result of DLS and AFM, it was demonstrated that both carrier peptides are formed into complexes and the sizes of the complexes clearly decrease with the N/P ratio increases.

Figure 3:
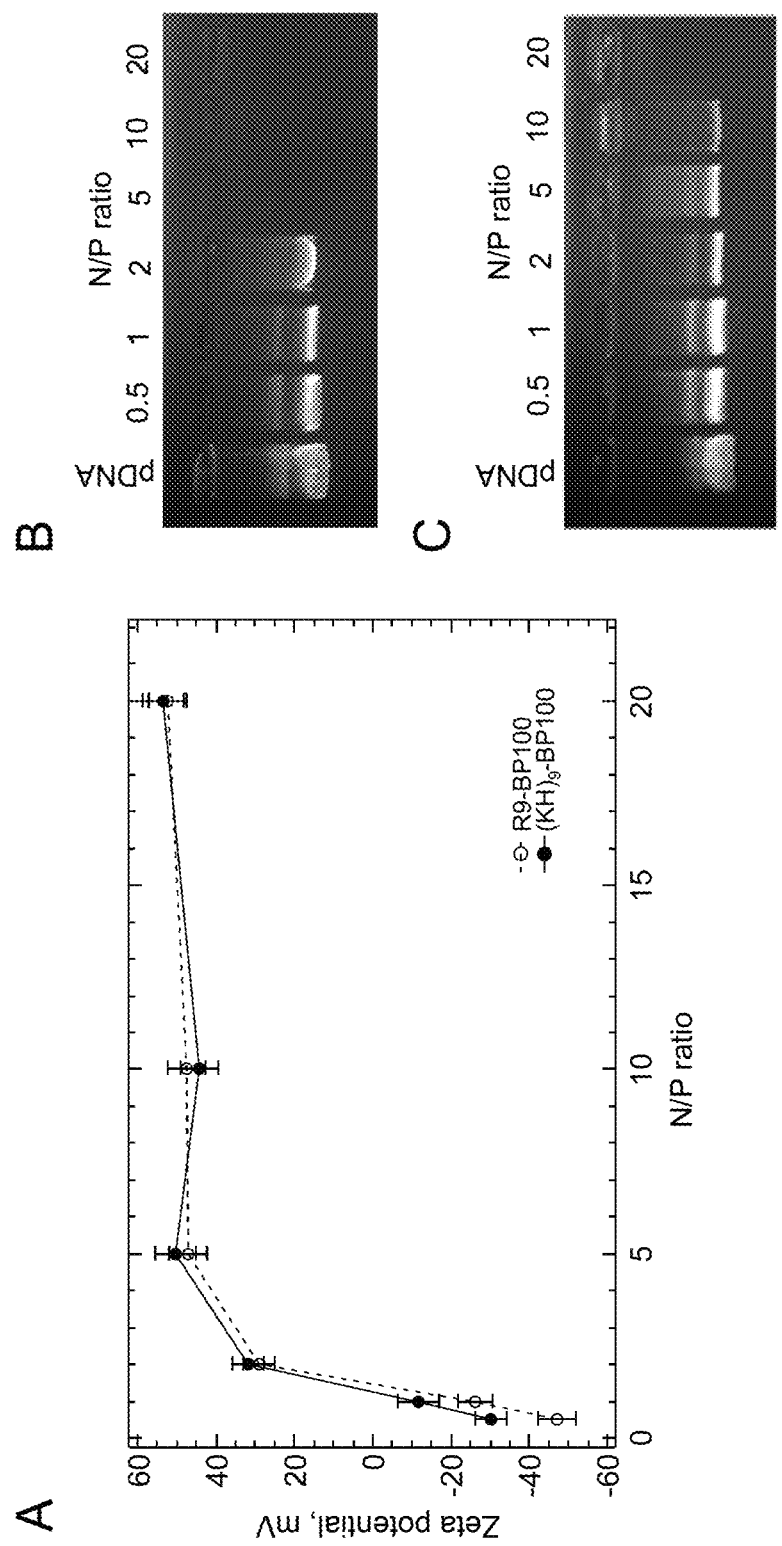
FIG. 3A shows the zeta potentials (measured) of R9-BP100-pDNA complexes and $(KH)_9$-BP100-pDNA complexes different in N/P ratio.
FIG. 3B and FIG. 3C show agarose gel electrophoretic results of R9-BP100-pDNA complexes (B) and $(KH)_9$-BP100-pDNA complexes (C) different in N/P ratio and pDNA alone.

The zeta potentials of both R9-BP100 and $(KH)_9$-BP100 pDNA complexes were negative values at an N/P ratio of 0.5 and 1, respectively; however, the zeta potentials of the complexes increased to positive values at an N/P ratio within the range of 2 to 20 (FIG. 3A). The zeta potential reached saturation at an N/P ratio of 5, meaning that the surface of the pDNA complexes was covered with a peptide. The ionic interaction and electrolytic stability of the complexes were evaluated by agarose gel electrophoresis and the results are shown in FIGS. 3B and C. An R9-BP100 complex prepared so as to have an N/P ratio of 0.5 to 2 showed the same mobility as that of a free pDNA (not complexed), i.e., the mobility of pDNA, in the agarose gel electrophoresis. The amount of pDNA that migrated decreased as the N/P ratio increased and no mobility was observed at an N/P ratio of 10 and 20. With an increase of the N/P ratio, the intensity of a band in a well became stronger, suggesting that pDNA was bound to a carrier peptide to form a stable complex. The $(KH)_9$-BP100 complex showed the same behavior; however, it was still observed that a small amount of pDNA migrated at an N/P ratio up to 10 (FIG. 3C). This explains that migration of pDNA (more specifically, migration of an R9-BP100 pDNA complex in the range of an N/P ratio of 0.5 to 5; and migration of a $(KH)_9$-BP100 pDNA complex in the range of an N/P ratio of 0.5 to 10) during agarose gel electrophoresis occurred since the complexes had a negative or low positive zeta potential. Although a complex with pDNA was still formed with a smaller amount of carrier peptide at a further lower N/P ratio, the complex failed to show sufficient stability during electrophoresis and pDNA was slightly liberated from a complex. In contrast, pDNA which formed a complex with a carrier peptide, was remained in a well. More stable pDNA complexes were formed by a further larger amount of peptide so as to have a further higher N/P ratio, and a larger number of pDNA complexes were fixed in a well; whereas the amount of pDNA released into agarose was low. Since the pI and molecular weight of R9-BP100 were 12.55 and 2827.56 Da, respectively; which are slightly different from the pI and molecular weight of (KH)$_9$-BP100 (10.81 and 3809.71 Da), the ionic interaction and stability of both complexes are different.

(Example 3) Treatment of Leaf with pDNA Complex

Benthamiana tobacco (*Nicotiana benthamiana*) leaf was selected as a target into which DNA is to be introduced by a carrier peptide-pDNA complex. This is because a leaf plays a complicated role in transforming the plant. A leaf contains rich resources including chromogen such as a chloroplast (widely used by plant biologists in order to attain stable transformation and temporary transformation (Pal Maliga, Annu Rev Plant Biol, 55, 289, 2004)), mitochondria (Val Romain, Eliza Wyszko, Clarisse Valentin et al., Nucleic Acids Res. 1 (13), 2011) and nuclei (Zouhair Elghabi, Stephanie Ruf, and Ralph Bock, The Plant Journal 67, 941, 2011).

In-vivo transfection experiment using the tobacco leaf was performed to evaluate an ability of a carrier peptide-pDNA complex to deliver a gene into plant cells through a cell wall. Complexes of pDNA encoding RLuc and GFP serving as a reporter gene with R9-BP 100 and (KH)$_9$-BP100 were directly allowed to permeate into *Nicotiana benthamiana* leaf. To determine the most efficient N/P ratio of a pDNA complex in the range of 0.1 to 20, a transfection efficiency is quantitatively characterized by use of RLuc assay.

A target plant was prepared as follows. Seeds of *benthamiana* tobacco were germinated in a pot containing a culture medium, which is a mixture of a soil (Pro-Mix) and vermiculite in a ratio of 2:1. The *benthamiana* tobacco plant was grown up to three weeks in a plant incubator (Biotron NK System) under constant light irradiation for 24 hours at a temperature of 29° C.

Leaves of *benthamiana* tobacco were sufficiently spread and directly impregnated with a solution (about 100 μL) of a complex comprising pDNA encoding green fluorescence protein (GFP) and *Renilla* luciferase (RLuc) by use of a syringe without a needle. The *benthamiana* tobacco plants thus treated were incubated in a plant incubator separately at a temperature of 29° C. and 21° C. under constant light irradiation for 16 hours per day until 6 days. To quantitatively evaluate RLuc gene expression, *Renilla* luciferase assay (Promega) was performed in accordance with the protocol provided by a manufacturer (n=4).

To be described in brief, sampling of the leaf impregnated was performed periodically in the range of 12 hours to 144 hours by cutting a square (1 cm$^2$) around an impregnated section. The samples each were lysed by use of *Renilla* Luciferase Assay Lysis Buffer (Promega). The lysate was briefly centrifuged and the supernatant was mixed with *Renilla* Luciferase Assay Substrate and *Renilla* Luciferase Assay Buffer (Promega). Gene expression was evaluated by a multi-mode microplate reader (Spectra MAX M3, Molecular Devices Corporation) based on the intensity (relative photometric unit) of photoluminescence. The amount of protein in the supernatant was determined by BCA protein assay (Pierce Biotechnology) to obtain a relative photometric unit/protein weight (RLU/mg). A transformant with RLuc gene-encoding pDNA via *Agrobacterium* (*Agrobacterium*) was used as a positive control in the experiment.

The statistical difference in transfection efficiency was determined by independent t-test using bilateral distribution. It was regarded that a statistically-significant difference is present at p<0.05. The data obtained in a cell survivability experiment are shown as an average±a standard deviation (n=4).

A complex prepared so as to have an N/P ratio of 0.1 failed to show significant transfection. In contrast, the transfection efficiency of a complex prepared so as to have an N/P ratio higher than 0.5 decreases with an increase of the N/P ratio. Both complexes of R9-BP100 and (KH)$_9$-BP100 prepared so as to have an N/P ratio of 0.5 showed the highest transfection efficiency compared to complexes having other N/P ratios (FIG. 4A). This means that excessive polycation induces cytotoxicity to a plant cell, decreasing transfection efficiency similarly to the case of animal cells (D. Fischer, T. Bieber, Y. Li et al., Pharm Res 16 (8), 1273, 1999).

According to the previous studies (K. Numata, J. Hamasaki, B. Subramanian et al., J Control Release 146 (1), 136, 2010; K. Numata and D. L. Kaplan, Biomacromolecules 11 (11), 3189, 2010; K. Numata, A. J. Mieszawska-Czajkowska, L. A. Kvenvold et al., Macromol Biosci, 2011; K. Numata, M. R. Reagan, R. H. Goldstein et al., Bioconjugate Chemistry 22 (8), 1605, 2011), a complex suitable for transfection into an animal cell was a smaller complex slightly positively charged. However, in this study, a carrier peptide-pDNA complex (negatively charged and having a diameter of about 300 nm) prepared so as to have an N/P ratio of 0.5 showed the highest transfection efficiency to a tobacco leaf. In consideration of the layer structure of cell wall and cell membrane, a relatively small and positively charged pDNA complex (N/P ratio larger than 2) is trapped in the cell wall due to ionic interaction and size effect, with the result that the transfection efficiency presumably decreased compared to a complex having an N/P ratio of 0.5.

The transfection efficiencies of complexes of R9-BP100-pDNA and (KH)$_9$-BP100-pDNA were measured at different time points to determine optimum incubation time for the gene delivery system of the present invention (FIG. 4B). The both pDNA complexes with R9-BP100 and (KH)$_9$-BP100 each showed the highest transfection efficiency in 12 hours and the transfection efficiency gradually reduces until 144 hours. From the results of the time-dependent change, it was demonstrated that the gene delivery performed by the carrier peptide of the present invention is an outstanding system for performing transfection in relatively short time. The cases of using R9-BP100 and (KH)$_9$-BP100 showed almost the same characteristics as a whole; however, they slightly differed in the time-dependent change of transfection efficiency (FIG. 4B), R9-BP100 showed quick and short transfection behavior compared to (KH)$_9$-BP100. The difference in transfection behavior is possibly because the decomposition of the (KH)$_9$ sequence (SEQ ID NO: 58) with protease in the cell is relatively slower compared to the decomposition of the R9 peptide (SEQ ID NO: 59). It should be noted that transfection behavior can be changed and controlled by selecting an appropriate amino acid sequence for the carrier peptide.

Figure 4:
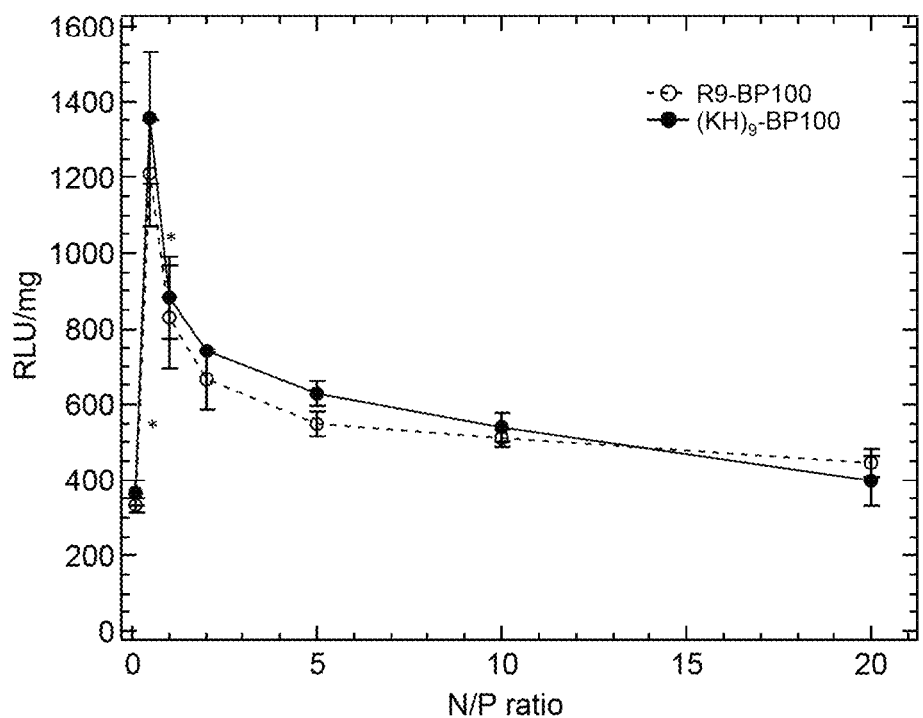
FIG. 4 shows Rluc expression results of a R9-BP100-pDNA complex and a $(KH)_9$-BP100-pDNA complex in tobacco leaves measured by varying N/P ratios (A) and incubation time period (B). The error bars indicate standard deviations of the samples (n=4). Significant difference was observed between two groups at *$p<0.05$.
Figure 4:
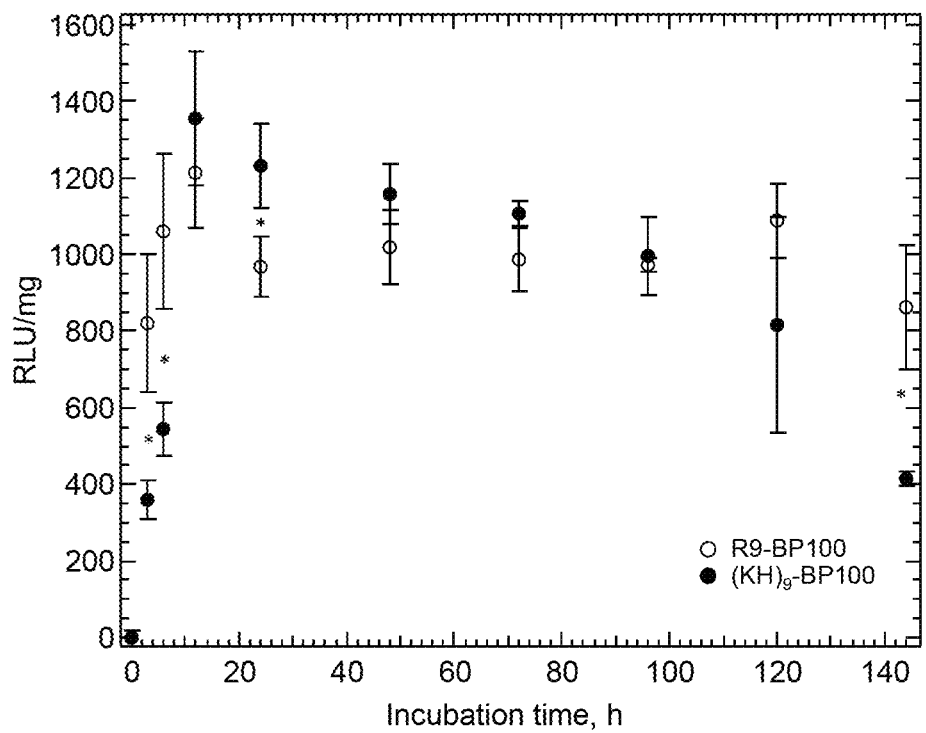

As a control experiment, pDNA was transfected to *benthamiana* tabacco leaf by use of cell-penetrating peptide, BP100 alone or polycation (KH)$_9$ (SEQ ID NO: 58) alone over 12 hours, using an N/P ratio of 0.5. As a result, 120±70 and 340±60 RLU/mg were respectively shown. These values were significantly low compared to the gene delivery by the carrier peptide of the present invention, as shown in FIG. 4. Based on the results of the controls, the carrier peptide of the present invention having a cell-penetrating sequence and a polycationic sequence in combination clearly enhances transfection efficiency about 12 times as high as the transfection efficiency of the cell-penetrating peptide alone. This is considered that DNA interacts with the polycationic sequence rather than the cell-penetrating sequence in the carrier peptide, with the result that the cell-penetrating sequence is preferentially present in the surface of the ionic complex and functionally permeates through a cell membrane.

Figure 5:
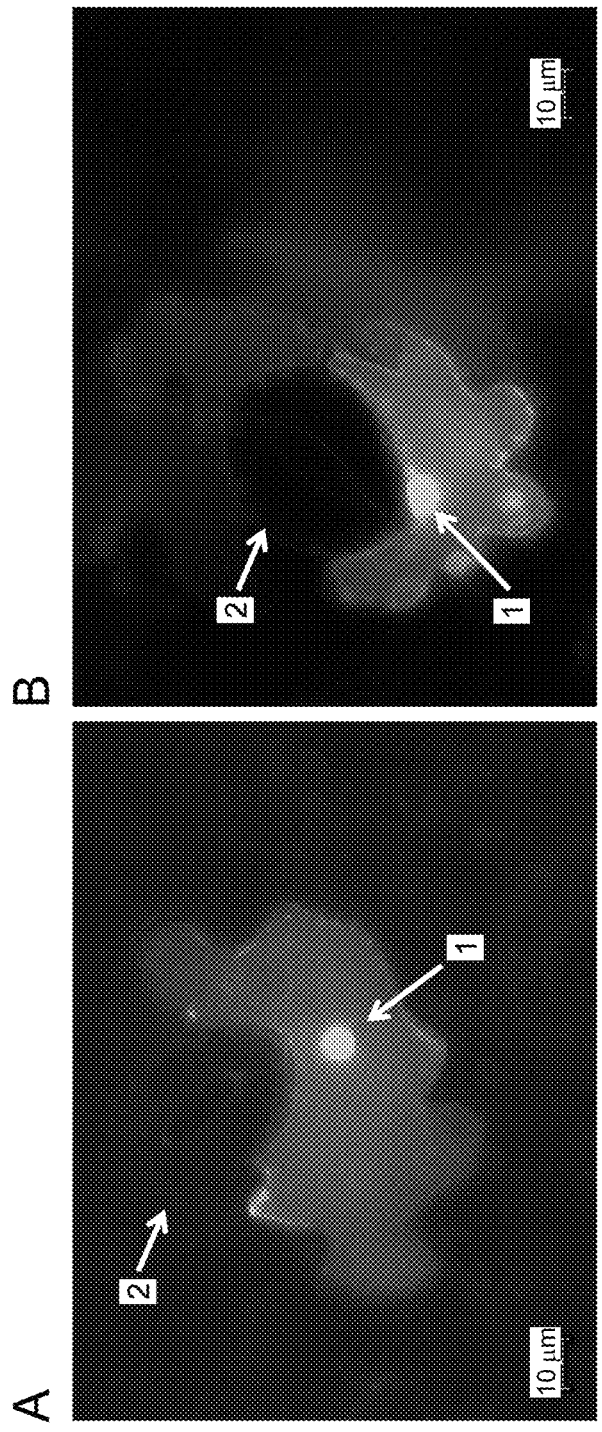
FIG. 5 shows fluorescent microscopic observation images of epidermal cells of *Nicotiana benthamiana* leaves expressing GFP genes, which are introduced by means of a R9-BP100-pDNA complex (A) and a $(KH)_9$-BP100-pDNA complex (B). Arrow (1) indicates a nucleus; whereas Arrow (2) indicates a guard cell.

To further investigate transfection behavior in a cell, *benthamiana* tobacco leaf transfection with a GFP-encoding pDNA was observed by a fluorescent microscope method. GFP expressed in the leaf was directly observed by a fluorescent microscope (Axio Observer Z1, 100× objective lens; Carl Zeiss) and an image was obtained by use of a CCD camera and AxioVision Rel 4.8 software (Carl Zeiss) (FIG. 5). The epidermal cell was impregnated with a complex solution and partially transfected by use of both peptides. When the interior of the cell was observed, the highest GFP expression was observed in the nucleus of the epidermal cell (FIG. 5, Arrow 1). The GFP expression in the nucleus demonstrates the transfection function of the gene delivery system of the present invention.

(Example 4) Preparation and Characterization of Carrier Peptide-dsRNA Complex

The complex of the carrier peptide ((KH)$_9$-BP100) synthesized in Example 1 and dsRNA was prepared. The size, surface charge, the secondary structure of the peptide and RNase resistance thereof were evaluated. Furthermore, an RNAi experiment in animal cell HEK was performed.

To synthesize siRNA, DNA oligonucleotides shown in the following table were designed (J. Y. Yu, S. L. DeRuiter, D. L. Turner, Proc Natl Acad Sci USA 99, 6047, 2002).

TABLE 2

| Primer | Sequence |
| --- | --- |
| T7-GFP5S-Fw | 5'-GGATCCTAATACGACTCACTATAGAAGCAGACGACTTCTTC-3' (SEQ ID NO: 35) |
| T7-GFP5S-Rev | 5'-AAGAAGAAGTCGTGCTGCTTCTATAGTGAGTCGTATTAGGATCC-3' (SEQ ID NO: 36) |
| T7-GFP5AntiS-Fw | 5'-GGATCCTAATACGACTCACTATAGAAGAAGTCGTGCTGCTTC-3' (SEQ ID NO: 37) |
| T7-GFP5AntiS-Rev | 5'-ATGAAGCAGCACGACTTCTTCTATAGTGAGTCGTATTAGGATCC-3' (SEQ ID NO: 38) |

Synthesis of siRNA was performed by use of T7 RiboMAX Express RNAi System (Promega). The RNA product was purified by QIAquick Nucleotide Removal kit (Qiagen) and isopropanol precipitation, and analyzed by 20% polyacrylamide gel electrophoresis using a siRNA marker (New England BioLabs). To form dsRNA (double stranded siRNA), a siRNA chain was heated at 95° C. for 5 minutes and subsequently cooled slowly to 25° C.

Two types of dsRNA, i.e., GFP5 siRNA silencing GFP expression and GL3 siRNA (Qiagen) silencing firefly luciferase (Luc) expression, were used. (Table 3).

TABLE 3

| RNA | Sequence |
| --- | --- |
| GFP5-sense | 5'-CUUCGUCGUGCUGAAGAAGUU-3' (SEQ ID NO: 39) |
| GFP5-antisense | 5'-CUUCUUCAGCACGACGAAGAU-3' (SEQ ID NO: 40) |
| Luc-sense | 5'-CUUACGCUGAGUACUUCGAdTdT-3' (SEQ ID NO: 41) |
| Luc-antisense | 5'-UCGAGGUACUCAGCGUAAGdTdT-3' (SEQ ID NO: 42) |

To prepare a carrier peptide-dsRNA complex, a carrier peptide (800 nM) was mixed with a dsRNA solution (400 nM) so as to satisfy carrier peptide/dsRNA molar ratios (0.5, 1, 2, 5, 10 and 20) at 25° C. The final dsRNA amount of each sample was set at 20 pmol. The complexes were characterized by a zeta potential meter, circular dichroism analysis (CD, J-820, JASCO) and an atomic force microscope (AFM). Measurement of a zeta potential, observation by the AFM and size (hydrodynamic diameter) measurement were performed in the same manner as in Example 2.

To analyze the secondary structure of the carrier peptide-dsRNA complex, CD spectra of the carrier peptide before and after a complex was formed with dsRNA, were measured at 25° C. The CD spectra were recorded at a speed of 12 nm·sec$^{-1}$ and a resolution of 1 nm, and scanned three times. The data were represented by residue molar ellipticity provided that the molecular weight and concentration of the carrier peptide were 3809.71 g/mol and 0.8 μM, respectively (FIG. 6C).

To evaluate RNase resistance of a complex, the complexes were treated with RNase (50 units, New England BioLabs) at 25° C. for 12 hours. After the RNase treatment, dsRNA was analyzed by agarose gel electrophoresis (1% agarose gel, TAE buffer, 100 V, 30 minutes) and stained with ethidium bromide (FIG. 6D).

To HEK cells were transfected with firefly luciferase-encoding pDNA by use of Lipofectamine 2000 (Invitrogen). After 6 hours, the medium was exchanged and dsRNA (20 pmol) and a carrier peptide were added. After the cells were incubated at 37° C. for 12 hours, luciferase assay was performed in order to evaluate luciferase gene expression (n=4). Using a multi-mode microplate reader (Spectra MAX M3; Molecular Devices Corporation), gene expression was evaluated based on the intensity of photoluminescence (relative photometric unit). The protein amount of each well was measured by BCA protein assay (Pierce Biotechnology) to obtain a relative photometric unit/protein weight (RLU/mg). A measurement value was shown by percentage relative to luciferase expression (Mock) in the cell treated with PBS (FIG. 6E). The statistical difference in luciferase assay was determined by independent t-test using bilateral distribution. It was regarded that a statistically-significant difference is present at $p<0.05$.

Figure 6:
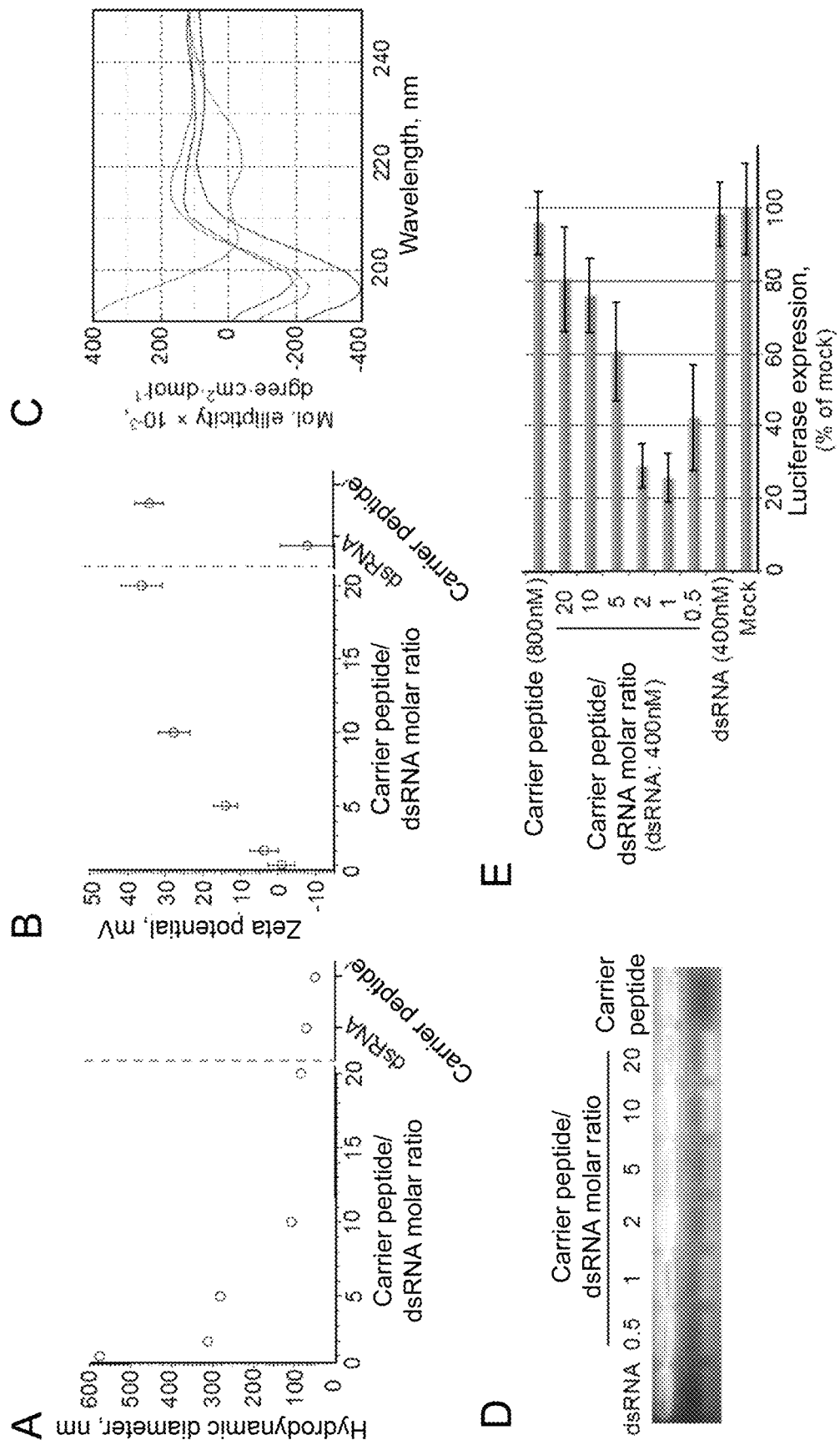
FIG. 6A shows the hydrodynamic diameters of dsRNA alone (400 nM), a carrier peptide alone (800 nM) and carrier peptide-dsRNA complexes comprising a carrier peptide and dsRNA in a molar ratio of 1 to 20.
FIG. 6B shows zeta potentials of dsRNA alone (400 nM), a carrier peptide alone (800 nM) and carrier peptide-dsRNA complexes comprising a carrier peptide and dsRNA in a different molar ratio (a molar ratio of a carrier peptide/dsRNA of 1 to 20).
FIG. 6C shows analysis results of a secondary structure based on the CD spectrum of a carrier peptide-dsRNA complex.
FIG. 6D shows the evaluation results of RNase resistance of a carrier peptide-dsRNA complex.
FIG. 6E shows the measurement results of gene silencing effect of the delivery system using a carrier peptide-dsRNA complex on dsRNA alone (400 nM), a carrier peptide alone (800 nM) and a complex comprising a carrier peptide and dsRNA (a molar ratio of 1 to 20). The silencing effect is obtained 12 hours after a complex is added.

The results are shown in FIG. 6A to FIG. 6E. In the case where the mixing molar ratio of dsRNA and a carrier peptide is 1:2, a carrier peptide-dsRNA complex having a diameter of about 300 nm and a small amount of positive surface charge was obtained (FIG. 6A-B). It was found that the secondary structure of the peptide changes from a helix to a random coil as the complex is formed (FIG. 6C). Furthermore, as the amount of carrier peptide increases, the peptide was protected from decomposition with RNase (FIG. 6D). The complex exhibits high resistance against RNase and a high possibility as an RNA carrier. In the RNAi test, a silencing efficiency of about 70% was shown and the highest silencing effect against luciferase was observed in a complex having carrier peptide and dsRNA in a molar ratio of 1 to 2 (FIG. 6E).

(Example 5) Treatment of *Arabidopsis thaliana* L. Leaf with a Carrier Peptide-dsRNA Complex An RNAi test for a leaf of *Arabidopsis thaliana* L. (*Arabidopsis thaliana*) in which YFP was excessively expressed, was performed using a complex composed of dsRNA and a carrier peptide ((KH)$_9$-BP 100) (mixing molar ratio of 1:2).

A YFP gene was introduced into *Agrobacterium* strain MP90, which was further introduced into a wild type *Arabidopsis thaliana* L. Seeds of the transgenic plant were collected. Seeds of wild type *Arabidopsis thaliana* L. and YFP transgenic *Arabidopsis thaliana* L. were germinated in a pot containing a culture medium, which is a mixture of soil (Pro-Mix) and vermiculite (2:1), and grown in a plant incubator (Biotron NK System) in light (16 hours)/dark (8 hours) conditions, at a temperature of 21° C.

Figure 7:
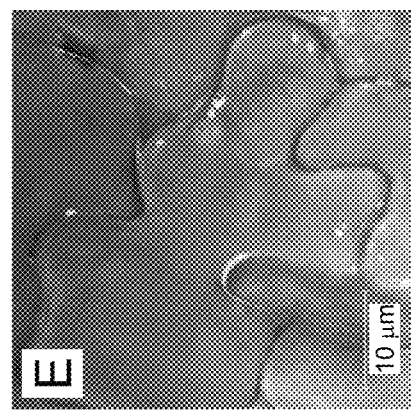
FIG. 7A (the upper portion) shows epidermal cells of *Arabidopsis thaliana* L. leaf before and after impregnated with a carrier peptide-dsRNA complex.
FIG. 7B shows YFP expression alone (yellow) of those shown in A.
FIG. 7C shows the results of Western blot analysis with YFP against lysates of *Arabidopsis thaliana* L. leaf before and after impregnated with a carrier peptide-dsRNA complex or a carrier peptide alone (control).
FIG. 7D shows the intensity of bands obtained in the Western blot shown in FIG. 7C.
FIG. 7E shows a CLSM image, which shows an intracellular distribution of a complex (orange) of Cy3-labelled dsRNA and a carrier peptide and nuclei (blue) stained with DAPI.
Figure 7:
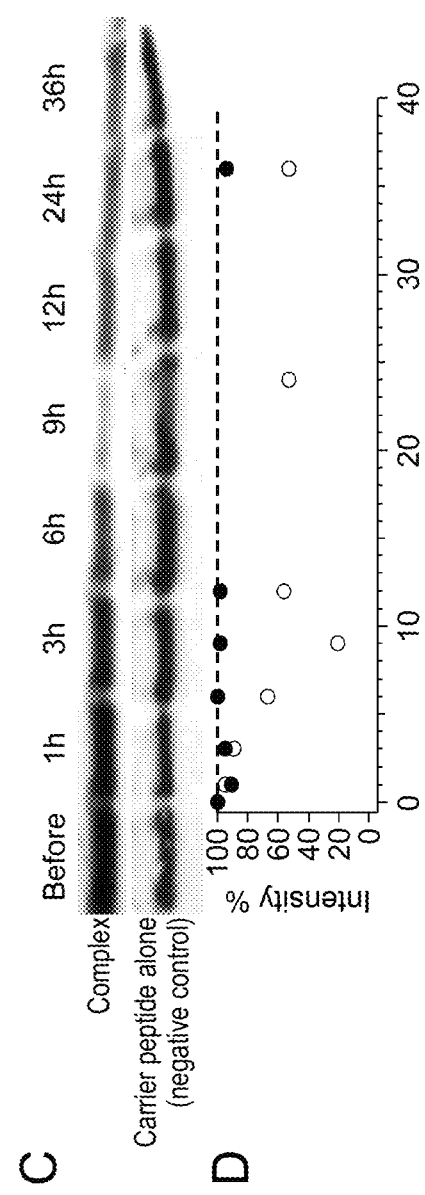

Leaves of *Arabidopsis thaliana* L. were sufficiently spread and directly impregnated with a solution (about 100 µL) of a complex comprising dsRNA (20 pmol) by use of a syringe without a needle (FIG. 7D). The *Arabidopsis thaliana* L. thus treated was incubated in a plant incubator up to 36 hours at a temperature of 21° C. under constant light irradiation for 16 hours per day.

Sampling of the leaf impregnated was performed by cutting a square (1 cm$^2$) around an impregnated section and lysed by use of *Renilla* Luciferase Assay Lysis Buffer (Promega). YFP gene expression was directly observed by a confocal laser scanning microscope (CLSM, Leica Microsystems). Labeling of dsRNA was made with Cy3. The leaf of *Arabidopsis thaliana* L. was impregnated with a complex of the labeled dsRNA (20 pmol) and (KH)$_9$-Bp100 (carrier peptide/dsRNA molar ratio: 2.0). After 12-hour incubation, the leaf was recovered, washed twice with PBS and incubated with a PBS solution (300 nM) of 4',6-diamidino-2-phenyl indole (DAPI, Lonza Walkersville, Inc.) for 10 minutes under vacuum (about 0.06 MPa). The intracellular distributions of the Cy3-labelled dsRNA-carrier peptide complex and nuclei stained with DAPI were observed by a CLSM at an excitation wavelength of 405 nm, 488 nm and 555 nm.

The leaf of *Arabidopsis thaliana* L. before and after RNAi, was washed with PBS, pulverized, lysed with a lysis buffer (Promega) and subjected to SDS polyacrylamide gel (PAGE) electrophoresis (Biorad). The protein separated was transferred to PVDF membrane (Invitrogen). A nonspecific bond was blocked by placing the transferred membrane to a 3% BSA solution in TBS. The membrane was incubated together with a primary antibody against YFP (Anti-GFP antibody [6AT316], Abcam), washed with TBS/0.1% Tween20, and subsequently, incubated together with a secondary antibody bound to a goat anti-mouse IgG AP conjugate (Novagen, Merck KGaA) at room temperature for one hour. Protein blots were treated with NBT and BCIP (Novagen) to emit color. Quantitative data of color intensity was obtained by use of Image J 1.46r (NIH, MD).

The results are shown in FIG. 7A to FIG. 7D. Silencing with YFP was clearly observed by CLSM. This result was also supported by quantitative analysis of Western blot. When microscopic observation and the results of Western blot are comprehensively examined, it was confirmed that RNAi of YFP most significantly occurred 9 hours to 12 hours after the complex was introduced into the leaf. When dsRNA was labeled with Cy3 and localization thereof within the cell was checked, it was observed that dsRNA was introduced around a nucleus or the like in the cell (FIG. 7E). From the above results, it was demonstrated that dsRNA can be easily introduced into a plant in a short time by using a carrier peptide as a dsRNA carrier.

(Example 6) Introduction of Giant DNA

A plasmid (80 kbp) encoding luciferase was prepared by use of *Bacillus subtilis* and introduced into *Arabidopsis thaliana* L. by use of a carrier peptide ((KH)$_9$-BP100). Twelve hours after introduction of the complex, luciferase was extracted from the leaf and subjected to quantitative analysis. As a result, efficient luciferase activity was confirmed. From the above results, it was demonstrated that giant gene (plasmid), which cannot be introduced by particle gun, etc., can be introduced by the gene introduction method using a carrier peptide.

(Example 7) Introduction of Organelle Selective Gene

A carrier peptide comprising a mitochondrial transit sequence (Cytochrome c oxidase subunit IV (yeast)) and a polycationic sequence was synthesized. In other words, (MLSLRQSIRFFKKHKHKHKHKHKHKHKHKH) (SEQ ID NO: 43) was synthesized by the solid phase peptide synthesis. The mitochondrial transit sequence is represented by MLSLRQSIRFFK (SEQ ID NO: 44) and the polycationic sequence is represented by KHKHKHKHKHKHKHKHKH) (SEQ ID NO: 22). Then, a complex was prepared from the carrier peptide synthesized and a plasmid vector (pDONRcox2p: rluc/gfp) that can function in mitochondria. In the same manner as in the above Examples, the complex was introduced into a leaf of *Arabidopsis thaliana* L. and expression of a reporter gene (*Renilla Luciferase*) in the mitochondria was quantitatively evaluated. Using a promoter (cox) which specifically functions in mitochondria, whether the complex was specifically introduced into the mitochondria was determined.

Figure 8:
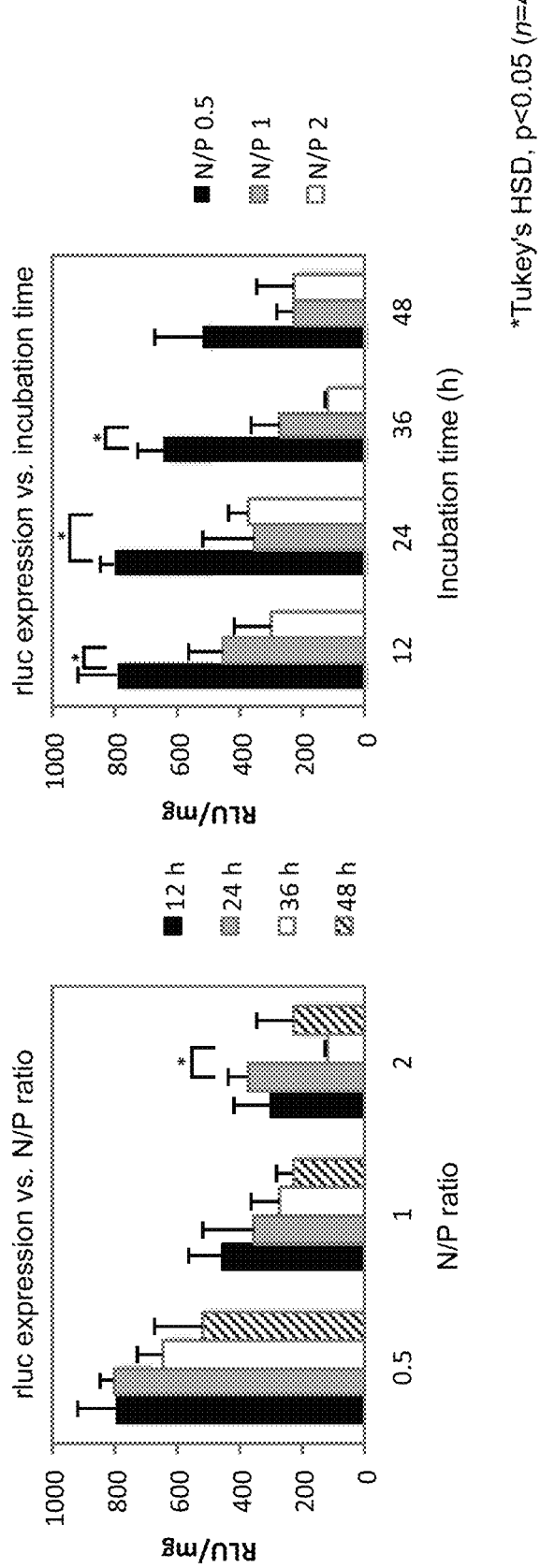
FIG. 8 (left) shows the results of Rluc expression in *Arabidopsis thaliana* L. to which a complex (which is prepared from a carrier peptide comprising a mitochondrial transit sequence and a plasmid comprising an Rluc gene in different N/P ratio) is introduced, in comparison with various N/P ratios.

The results are shown in FIG. 8A to FIG. 8B. The effect of a mixing ratio (N/P=0.5, 1 and 2) of the carrier peptide and the plasmid on the gene introduction efficiency to mitochondria was evaluated. As a result, a highly significant difference was shown at N/P=0.5 (FIG. 8A). When the change of gene introduction efficiency with time was checked, high gene expression was confirmed at a time point from 12 hours to 24 hours after the introduction (FIG. 8B). From the above results, it was demonstrated that the organelle-specific gene introduction can be made in a relatively short time (from 12 hours to 24 hours) by adding an organelle transit sequence to a carrier peptide sequence.

INDUSTRIAL APPLICABILITY

Owing to the present invention, various plant species can be easily used in substance production technique and a novel plant capable of producing a bio-substance such as a bio-plastic and bio-fuel from carbon dioxide can be created. Owing to the present invention, production technique for not only bio-substances but also substances in a wide variety of fields including proteins for medicinal drugs, foods, energy substances can be substituted by the novel production technique using plants and carbon dioxide, and construction of a novel bio-industry and low-carbon society can be simultaneously realized.

All publications, patents and Patent Applications cited in the specification are incorporated in their entirety in the specification by reference.

The invention claimed is:

1. A method of introducing a nucleic acid into a target plant cell, comprising:

forming a complex by bringing a carrier peptide into contact with a nucleic acid, wherein the carrier peptide comprises (i) a cell-penetrating sequence selected from the group consisting of each of SEQ ID NOs:1-20, MPG, and Pep-1 and (ii) a polycationic sequence selected from the group consisting of a continuous series of 5 or more and 20 or less lysine (K) residues (SEQ ID NO: 60), a continuous series of 5 or more and 20 or less arginine (R) residues (SEQ ID NO: 61), a continuous series of 5 or more and 20 or less histidine (H) residues (SEQ ID NO: 62), 3 to 20 repeat sequences of KH (SEQ ID NO: 45), and 3 to 20 repeat sequences of RH (SEQ ID NO: 63), wherein the ratio of the number of amine groups in the carrier peptide and the number of phosphate groups in the nucleic acid (N/P ratio) is 0.2 or more and no more than 2, and bringing the obtained complex into contact with a target plant cell.

2. The method according to claim 1, wherein the complex has an average hydrodynamic diameter of 150 to 500 nm.

3. The method according to claim 1, wherein forming the complex is performed in the presence of a second carrier peptide comprising an organelle transit sequence selected from the group consisting of each of SEQ ID NOs:23-29 and SEQ NO:44 and a polycationic sequence selected from the group consisting of a continuous series of 5 or more lysine and 20 or less (K) residues (SEQ ID NO: 60), a continuous series of 5 or more and 20 or less arginine (R) residues (SEQ ID NO: 61), a continuous series of 5 or more and 20 or less histidine (H) residues (SEQ ID NO: 62), 3 to 20 repeat sequences of KH (SEQ ID NO: 45), and 3 to 20 repeat sequences of RH (SEQ ID NO: 63).

4. The method according to claim 1, wherein the carrier peptide further comprises an organelle transit sequence selected from the group consisting of each of SEQ ID NOs:23-29 and SEQ ID NO:44.

5. The method according to claim 1, wherein incubation time for bringing the complex into contact with a target plant cell is 5 to 150 hours.

6. A complex for introducing a nucleic acid into a target plant cell, comprising:

a carrier peptide comprising (i) a plant cell-penetrating sequence selected from the group consisting of each SEQ ID NOs:1-20, MPG, and Pep-1 and (ii) a polycationic sequence selected from the group consisting of a continuous series of 5 or more and 20 or less lysine (K) residues (SEQ ID NO: 60), a continuous series of 5 or more and 20 or less arginine (R) residues (SEQ ID NO: 61), a continuous series of 5 or more and 20 or less histidine (H) residues (SEQ ID NO: 62), 3 to 20 repeat sequences of KH (SEQ ID NO: 45), and 3 to 20 repeat sequences of RH (SEQ ID NO: 63), and a nucleic acid, wherein the ratio of the number of amine groups in the carrier peptide and the number of phosphate groups in the nucleic acid (N/P ratio) is 0.2 or more and no more than 2.

7. The complex according to claim 6, further comprising an organelle transit sequence selected from the group consisting of each of SEQ ID NOs:23-29 and SEQ ID NO:44.

8. The complex according to claim 6, further comprising a second carrier peptide comprising (i) an organelle transit sequence selected from the group consisting of each of SEQ ID NOs:23-29 and SEQ ID NO:44 and (ii) a polycationic sequence selected from the group consisting of a continuous series of 5 or more and 20 or less lysine (K) residues (SEQ ID NO: 60), a continuous series of 5 or more and 20 or less arginine (R) residues (SEQ ID NO: 61), a continuous series of 5 or more and 20 or less histidine (H) residues (SEQ ID NO: 62), 3 to 20 repeat sequences of KH (SEQ ID NO: 45), and 3 to 20 repeat sequences of RH (SEQ ID NO: 63).

9. The complex according to claim 6, wherein the complex has an average hydrodynamic diameter of 150 to 300 nm.

10. The method of claim 1, wherein the cell-penetrating sequence is selected from the group consisting of SEQ ID NOs: 1-20, and the polycationic sequence is RRRRRRRRR (SEQ ID NO: 59), SEQ ID NO: 21 or SEQ ID NO: 22.

11. The complex of claim 6, wherein the cell-penetrating sequence is selected from the group consisting of SEQ ID NOs: 1-20, and the polycationic sequence is RRRRRRRRR (SEQ. ID NO: 59), SEQ ID NO: 21 or SEQ ID NO: 22.

* * * * *

```
                          SEQUENCE LISTING

<160> NUMBER OF SEQ ID NOS: 63

<210> SEQ ID NO 1
    <211> LENGTH: 11
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 1

Lys Lys Leu Phe Lys Lys Ile Leu Lys Tyr Leu
    1               5                   10

<210> SEQ ID NO 2
    <211> LENGTH: 18
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 2

Arg Lys Lys Arg Arg Gln Arg Arg Arg Lys Lys Arg Arg Gln Arg
    1               5                   10                  15

Arg Arg

<210> SEQ ID NO 3
    <211> LENGTH: 9
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 3

Arg Lys Lys Arg Arg Gln Arg Arg Arg
    1               5

<210> SEQ ID NO 4
    <211> LENGTH: 12
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 4

Pro Leu Ser Ser Ile Phe Ser Arg Ile Gly Asp Pro
    1               5                   10

<210> SEQ ID NO 5
    <211> LENGTH: 12
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 5
```

```
Pro Ile Ser Ser Ile Phe Ser Arg Thr Gly Asp Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ile Ser Ser Ile Leu Ser Lys Thr Gly Asp Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Ile Leu Ser Ile Phe Ser Lys Ile Gly Asp Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Leu Ser Ser Ile Phe Ser Lys Ile Gly Asp Pro
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Leu Ser Ser Ile Phe Ser His Ile Gly Asp Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Leu Ser Ser Ile Phe Ser Ser Ile Gly Asp Pro
1               5                   10

<210> SEQ ID NO 11
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Val Ala Leu Leu Pro Ala Val Leu Leu Ala Leu Leu Ala Pro
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Val Leu Leu Pro Val Leu Leu Ala Ala Pro
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Thr Val Leu Ala Leu Gly Ala Leu Ala Gly Val Gly Val Gly
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gly Ala Leu Phe Leu Gly Trp Leu Gly Ala Ala Gly Ser Thr Met Gly
1               5                   10                  15

Ala

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Gly Leu Gly Leu His Leu Leu Val Leu Ala Ala Ala Leu Gln Gly
1               5                   10                  15

Ala

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Leu Ala Leu Lys Leu Ala Leu Lys Ala Leu Lys Ala Ala Leu Lys
1               5                   10                  15

Leu Ala

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 21

Arg Arg Arg Arg Arg Arg
1               5

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys His Lys His Lys His Lys His Lys His Lys His Lys His Lys His
1               5                   10                  15

Lys His

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Met Ala Met Arg Ser Thr Phe Ala Ala Arg Val Gly Ala Lys
1               5                   10                  15

Pro Ala Val Arg Gly Ala Arg Pro Ala Ser Arg Met Ser Cys Met Ala
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gln Val Thr Met Lys Ser Ser Ala Val Ser Gly Gln Arg Val Gly
1               5                   10                  15

Gly Ala Arg Val Ala Thr Arg Ser Val Arg Arg Ala Gln Leu Gln Val
            20                  25                  30

<210> SEQ ID NO 25
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ala Thr Met Val Ala Gly Ile Ser Leu Arg Gly Pro Val Met Ser
1               5                   10                  15

Ser His Arg Thr Phe Ser Val Thr Lys Arg Ala Ser Leu Pro Gln Ser
            20                  25                  30

Lys Leu Ser Ser Glu Leu Ser Phe Val Thr Ser Gln Leu Ser Gly Leu
        35                  40                  45

Lys Ile Ser Ser Thr His Phe Ile Ser Ser Ala Pro Leu Ser Val
    50                  55                  60

Pro Phe Lys Pro Ser Leu Gln Pro Val Ala
65                  70

<210> SEQ ID NO 26
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Ala Leu Gln Ser Ser Phe Ala Gly Leu Ser Thr Ser Phe Phe
1               5                   10                  15

Gly Gln Arg Phe Ser Pro Pro Leu Ser Leu Pro Pro Leu Val Lys Ser
            20                  25                  30

Thr Glu Gly Pro Cys Leu Ile Gln Ala
        35                  40

<210> SEQ ID NO 27
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ala Val Ser Phe Ser Leu Val Gly Ala Phe Lys Gly Leu Ser Leu
1               5                   10                  15

Ala Ser Ser Ser Ser Phe Leu Lys Gly Asp Phe Gly Ala Ala Phe Pro
            20                  25                  30

Val Ala Pro Lys Phe Ser Val Ser Phe Pro Leu Lys Ser Pro Leu Thr
        35                  40                  45

Ile Glu Ser
    50

<210> SEQ ID NO 28
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 29

Met Ala Ala Ser Thr Met Ala Leu Ser Ser Pro Ala Phe Ala Gly Lys
1               5                   10                  15

Ala Val Lys Leu Ser Pro Ala Ala Ser Glu Val Leu Gly Ser Gly Arg
            20                  25                  30

Val Thr Met Arg Lys Thr Val
        35

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Arg Arg Arg Arg Arg Arg Lys Lys Leu Phe Lys Lys Ile
1               5                   10                  15

Leu Lys Tyr Leu
        20

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys His Lys His Lys His Lys His Lys His Lys His Lys His Lys His
1               5                   10                  15

Lys His Lys Lys Leu Phe Lys Lys Ile Leu Lys Tyr Leu
            20                  25

<210> SEQ ID NO 32
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Arg Arg Arg Arg Arg Arg Arg Lys Lys Arg Arg Gln Arg
1               5                   10                  15

Arg Arg Arg Lys Lys Arg Arg Gln Arg Arg Arg
            20                  25

<210> SEQ ID NO 33
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ala Met Ala Met Arg Ser Thr Phe Ala Ala Arg Val Gly Ala Lys
1               5                   10                  15

Pro Ala Val Arg Gly Ala Arg Pro Ala Ser Arg Met Ser Cys Met Ala
            20                  25                  30
```

```
Lys His Lys His Lys His Lys His Lys His Lys His Lys His Lys His
        35                  40                  45

Lys His
    50

<210> SEQ ID NO 34
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Gln Val Thr Met Lys Ser Ser Ala Val Ser Gly Gln Arg Val Gly
1               5                   10                  15

Gly Ala Arg Val Ala Thr Arg Ser Val Arg Arg Ala Gln Leu Gln Val
            20                  25                  30

Lys His Lys His Lys His Lys His Lys His Lys His Lys His Lys His
        35                  40                  45

Lys His
    50

<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggatcctaat acgactcact atagaagcag acgacttctt c                          41

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aagaagaagt cgtgctgctt ctatagtgag tcgtattagg atcc                       44

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggatcctaat acgactcact atagaagaag tcgtgctgct tc                         42

<210> SEQ ID NO 38
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
```

```
atgaagcagc acgacttctt ctatagtgag tcgtattagg atcc                    44
```

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      GFP5 siRNA oligonucleotide

<400> SEQUENCE: 39

```
cuucgucgug cugaagaagu u                                             21
```

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      GFP5 siRNA oligonucleotide

<400> SEQUENCE: 40

```
cuucuucagc acgacgaaga u                                             21
```

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      GL3 siRNA oligonucleotide
<220> FEATURE:
<223> OTHER INFORMATION: Description of Combined DNA/RNA Molecule:
      Synthetic GL3 siRNA oligonucleotide
<220> FEATURE:
<221> NAME/KEY: misc_RNA
<222> LOCATION: (1)..(19)

<400> SEQUENCE: 41

```
cuuacgcuga guacuucgat t                                             21
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      GL3 siRNA oligonucleotide
<220> FEATURE:
<223> OTHER INFORMATION: Description of Combined DNA/RNA Molecule:
      Synthetic GL3 siRNA oligonucleotide
<220> FEATURE:
<221> NAME/KEY: misc_RNA
<222> LOCATION: (1)..(19)

<400> SEQUENCE: 42

```
ucgagguacu cagcguaagt t                                             21
```

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Met Leu Ser Leu Arg Gln Ser Ile Arg Phe Phe Lys Lys His Lys His
1               5                   10                  15
```

Lys His Lys His Lys His Lys His Lys His Lys His
        20                  25                  30

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Leu Ser Leu Arg Gln Ser Ile Arg Phe Phe Lys
1               5                   10

<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 3-20 "Lys His"
      repeating units

<400> SEQUENCE: 45

Lys His Lys His Lys His Lys His Lys His Lys His Lys His Lys His
1               5                   10                  15

Lys His Lys His Lys His Lys His Lys His Lys His Lys His Lys His
            20                  25                  30

Lys His Lys His Lys His Lys His
        35                  40

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 3-20 residues

<400> SEQUENCE: 46

Arg Arg Arg Arg Arg Arg Arg Arg Arg Arg Arg Arg Arg Arg Arg Arg
1               5                   10                  15

Arg Arg Arg Arg
            20

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Arg Arg Arg Arg Arg Arg
1               5

```
<210> SEQ ID NO 48
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 5-15 "Lys His"
      repeating units

<400> SEQUENCE: 48

Lys His Lys His Lys His Lys His Lys His Lys His Lys His Lys His
1               5                   10                  15

Lys His Lys His Lys His Lys His Lys His Lys His Lys His
            20                  25                  30

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(24)
<223> OTHER INFORMATION: This sequence may encompass 7-12 "Lys His"
      repeating units

<400> SEQUENCE: 49

Lys His Lys His Lys His Lys His Lys His Lys His Lys His Lys His
1               5                   10                  15

Lys His Lys His Lys His Lys His
            20

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 50

Arg Arg Arg Arg Arg Arg Arg Arg Arg Arg Arg Arg Arg Arg Arg
1               5                   10                  15

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: This sequence may encompass 7-12 residues

<400> SEQUENCE: 51

Arg Arg Arg Arg Arg Arg Arg Arg Arg Arg Arg Arg
1               5                   10
```

```
<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 3-20 residues

<400> SEQUENCE: 52

Lys Lys Lys Lys Lys Lys Lys Lys Lys Lys Lys Lys Lys Lys Lys Lys
1               5                   10                  15

Lys Lys Lys Lys
            20

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 53

Lys Lys Lys Lys Lys Lys Lys Lys Lys Lys Lys Lys Lys Lys Lys
1               5                   10                  15

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: This sequence may encompass 7-12 residues

<400> SEQUENCE: 54

Lys Lys Lys Lys Lys Lys Lys Lys Lys Lys Lys Lys
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 3-20 residues

<400> SEQUENCE: 55

His His His His His His His His His His His His His His His His
1               5                   10                  15

His His His His
            20
```

```
<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 56

His His His His His His His His His His His His His His His
1               5                   10                  15

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: This sequence may encompass 7-12 residues

<400> SEQUENCE: 57

His His His His His His His His His His His His
1               5                   10

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys His Lys His Lys His Lys His Lys His Lys His Lys His Lys His
1               5                   10                  15

Lys His

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Arg Arg Arg Arg Arg Arg Arg Arg
1               5

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 5-20 residues

<400> SEQUENCE: 60
```

```
Lys Lys Lys Lys Lys Lys Lys Lys Lys Lys Lys Lys Lys Lys Lys
1               5                   10                  15

Lys Lys Lys Lys
            20
```

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 5-20 residues

<400> SEQUENCE: 61

```
Arg Arg Arg Arg Arg Arg Arg Arg Arg Arg Arg Arg Arg Arg Arg
1               5                   10                  15

Arg Arg Arg Arg
            20
```

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 5-20 residues

<400> SEQUENCE: 62

```
His His His His His His His His His His His His His His His
1               5                   10                  15

His His His His
            20
```

<210> SEQ ID NO 63
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 3-20 "Arg His"
      repeating units

<400> SEQUENCE: 63

```
Arg His Arg His Arg His Arg His Arg His Arg His Arg His Arg His
1               5                   10                  15

Arg His Arg His Arg His Arg His Arg His Arg His Arg His Arg His
            20                  25                  30

Arg His Arg His Arg His Arg His
        35                  40
```